United States Patent [19]

Battocletti et al.

[11] Patent Number: 4,613,818
[45] Date of Patent: Sep. 23, 1986

[54] NUCLEAR MAGNETIC RESONANCE BLOOD FLOWMETER

[75] Inventors: Joseph H. Battocletti, River Hills; Richard E. Halbach, Brookfield; Frederick J. Antonich; Anthony Sances, Jr., both of Milwaukee; Thomas A. Knox, Brookfield, all of Wis.

[73] Assignee: The Medical College of Wisconsin, Inc., Milwaukee, Wis.

[21] Appl. No.: 505,686

[22] Filed: Jun. 20, 1983

[51] Int. Cl.$^4$ ............... G01N 24/06; G01N 24/08; G01R 33/22
[52] U.S. Cl. ................ 324/306; 324/224; 324/309; 324/320
[58] Field of Search ............ 324/306, 308, 309, 313, 324/315, 320, 224, 225, 251, 314

[56] References Cited

U.S. PATENT DOCUMENTS

| | | | |
|---|---|---|---|
| 3,331,972 | 7/1967 | Möller | 338/32 H |
| 3,419,793 | 12/1968 | Genthe et al. | 324/306 |
| 3,419,795 | 12/1968 | Genthe et al. | 324/306 |
| 3,473,108 | 10/1969 | McCormick | 324/306 |
| 3,551,794 | 12/1970 | Vander Heyden et al. | 324/306 |
| 3,559,044 | 1/1971 | Vander Heyden et al. | 324/306 |
| 3,670,239 | 6/1972 | Shiraiwa et al. | 324/235 |
| 3,932,805 | 1/1976 | Abe et al. | 324/309 |
| 4,319,190 | 3/1982 | Brown | 324/309 |
| 4,327,416 | 4/1982 | Jerrim | 324/251 |
| 4,339,716 | 7/1982 | Young | 324/309 |
| 4,339,717 | 7/1982 | Tsuda et al. | 324/313 |
| 4,339,718 | 7/1982 | Bull | 324/317 |
| 4,345,207 | 8/1982 | Bertrand et al. | 324/308 |
| 4,354,157 | 10/1982 | Feiner | 324/312 |
| 4,354,499 | 10/1982 | Damadian | 128/653 |
| 4,371,837 | 2/1983 | Sieverin | 324/225 |
| 4,442,404 | 4/1984 | Bergmann | 324/315 |
| 4,475,084 | 10/1984 | Moore et al. | 324/309 |

FOREIGN PATENT DOCUMENTS 0021363 2/1979 Japan ................ 324/224

OTHER PUBLICATIONS

Battocletti et al, "A Nuclear Magnetic Resonance Noninvasive Leg Blood Flowmeter", IEEE 1981 Frontiers of Engineering in Health Care, Houston, Texas, Sep. 1981, pp. 145-147.

Halbach et al, "Blood Flow Imaging Techniques Using NMR", IEEE 1982 Frontiers of Engineering in Health Care, Philadelphia, PA, Sep. 1982.

"NMR Diffusion and Flow Measurements and an Introduction to Spin Phase Graphing", J. R. Singer, *The Institute of Physics,* 1978, pp. 281-291.

(List continued on next page.)

*Primary Examiner*—Stewart J. Levy
*Assistant Examiner*—Kevin D. O'Shea
*Attorney, Agent, or Firm*—Barry E. Sammons

[57] ABSTRACT

Blood flow in human limbs is measured non-invasively by a nuclear magnetic resonance blood flowmeter which includes a pair of polarizing magnets whose fields are stabilized by electromagnets in each pole piece that are energized in accordance with the magnetic flux of the magnets as sensed by a Hall effect sensor. Blood molecules are either self-tagged by the polarizing field or are separately tagged by a tag coil whose field is orthogonal to the polarizing field. Once tagged, the variation in the magnetic moment of the molecule due to the tagging is detected by the variation in voltage in the receiver coil which is located orthogonally to the transmitter coil so as to reduce crosscoupling therebetween. Two sets of scanner coils, one located parallel to and the other orthogonal to the polarizing field directions, respectively, are energized to create a pair of intersecting null planes which act to cancel nuclear magnetic resonance response detected by the receiver everywhere but along the line where the two null planes intersect. By varying the current in the scanner coils, the resulting line of intersection of the null planes can be moved in two dimensions so as to scan the limb thereby allowing blood flow measurement at various locations within the limb.

20 Claims, 20 Drawing Figures

OTHER PUBLICATIONS

"Cerebral Blood Flow Measurement: NMR Flat Crossed Coil Probe"-J. H. Battocletti et al, Conference Record, 31st Annual Conference of Engineering, Medicine Biology Alliance, Atlanta, GA, 1978, p. 79.

"Synchronized Detection of Upper Extremity Blood Flow Signals in a NMR Flowmeter", R. E. Halbach et al, Conference Recorporation Engineering Medicine and Biology Alliance, Atlanta, GA, 1978, p. 73.

"Flat Crossed Coil Detector for Blood Flow Measurement Using Nuclear Magnetic Resonance", J. H. Battocletti et al, *Medical and Biological Engineering and Computing*, Mar. 1979, pp. 183-191.

"Cylindrical Crossed-Coil NMR Limb Blood Flowmeter", R. E. Halbach et al, *Review of Scientific Instruments*, vol. 50, No. 4, (1979) pp. 428-434.

"Clinical Applications of the Nuclear Magnetic Resonance (NMR) Limb Blood Flowmeter", J. H. Battocletti et al, Proceedings of the IEEE, vol. 67, No. 9, Sep., 1979, pp. 1359-1361.

Nuclear Magnetic Resonance (NMR) Cylindrical Blood Flowmeter: In Vitro Evaluation, S. X. Salles-Cuhna et al, Journal of Clinical Engineering, vol. 5, No. 3, Jul.-Sep. 1980, pp. 205-213.

"Ranging for Individual Artery Flow in the Nuclear Resonance Flowmeter", R. E. Halbach et al, Conference Record, IEEE Frontier of Engineering in Health Care, Washington, D.C., Sep. 1980, pp. 356-359.

"Blood Flow Detection Using the Flat Crossed-Coil Nuclear Magnetic Resonance Flowmeter", R. E. Halbach et al, *IEEE Transactions on Biomedical Engineering*, vol. BME-28, No. 1, Jan. 1981, pp. 40-42.

"Nuclear Magnetic Resonance Techniques Applied to Noninvasive Measurement of Blood Flow", R. E. Halbach et al, Conference Record Proceedings of the International Cardiovascular Congress III, Scottsdale, AZ, Feb. 16-18, 1981, p. 1-11.

"Noninvasive Measurement of Blood Flow by Nuclear Magnetic Resonance (NMR) Techniques", R. E. Holbach et al, Proceedings IIId Congress of International Society for Artificial Organs, Paris, France, Jul. 1981, pp. 1-13.

Noninvasive Measurement of Blood Flow by Nuclear Magnetic Resonance (NMR) Techniques, R. E. Halbach et al, *Artificial Organs*, 5A:25, Jul. 1981, p. 25.

"Techniques for Measurement of Regional Cerebral Blood Flow Using NMR", R. E. Halbach et al, *IEEE* 1981 *Frontiers of Engineering in Health Care*, Houston, Texas, Sep. 1981, pp. 159-162.

"The NMR Blood Flowmeter-Theory and History", Joseph H. Battocletti, *Journal of Medical Physics*, Jul.-/Aug. 1981, pp. 435-457.

"The NMR Blood Flowmeter-Design", R. E. Halbach et al, *Journal of Medical Physics*, Jul./Aug. 1981, pp. 444-451.

"The NMR Blood Flowmeter-Applications", S. X. Salles-Cunha et al, *Journal of Medical Physics*, Jul./Aug. 1981, pp. 452-458.

"Blood Flow Imaging Techniques Using NMR", R. E. Halbach et al, IEEE 1982 Frontiers of Engineering in Health Care, Sep. 1982, Philadelphia, PA.

FIELD REGULATOR
CIRCUIT
48b

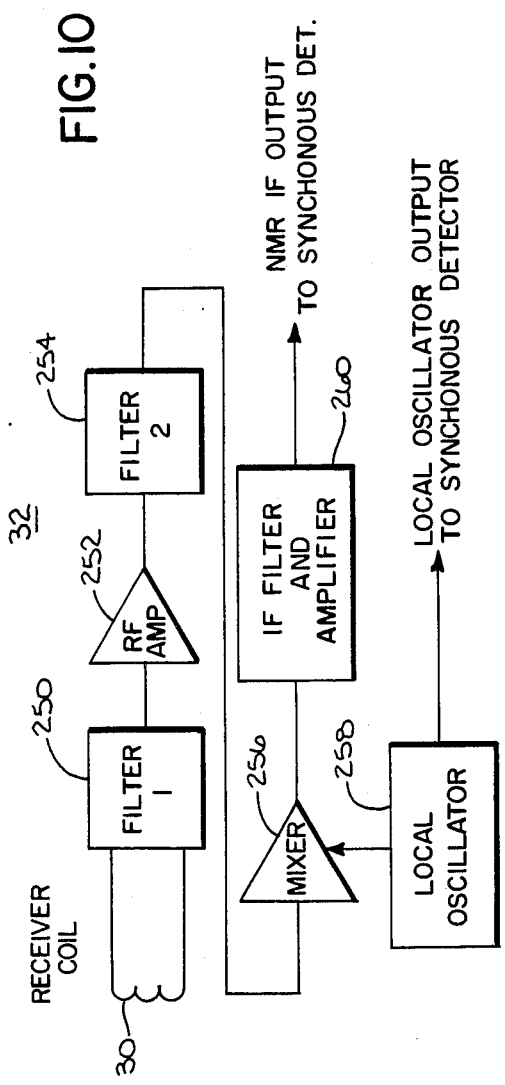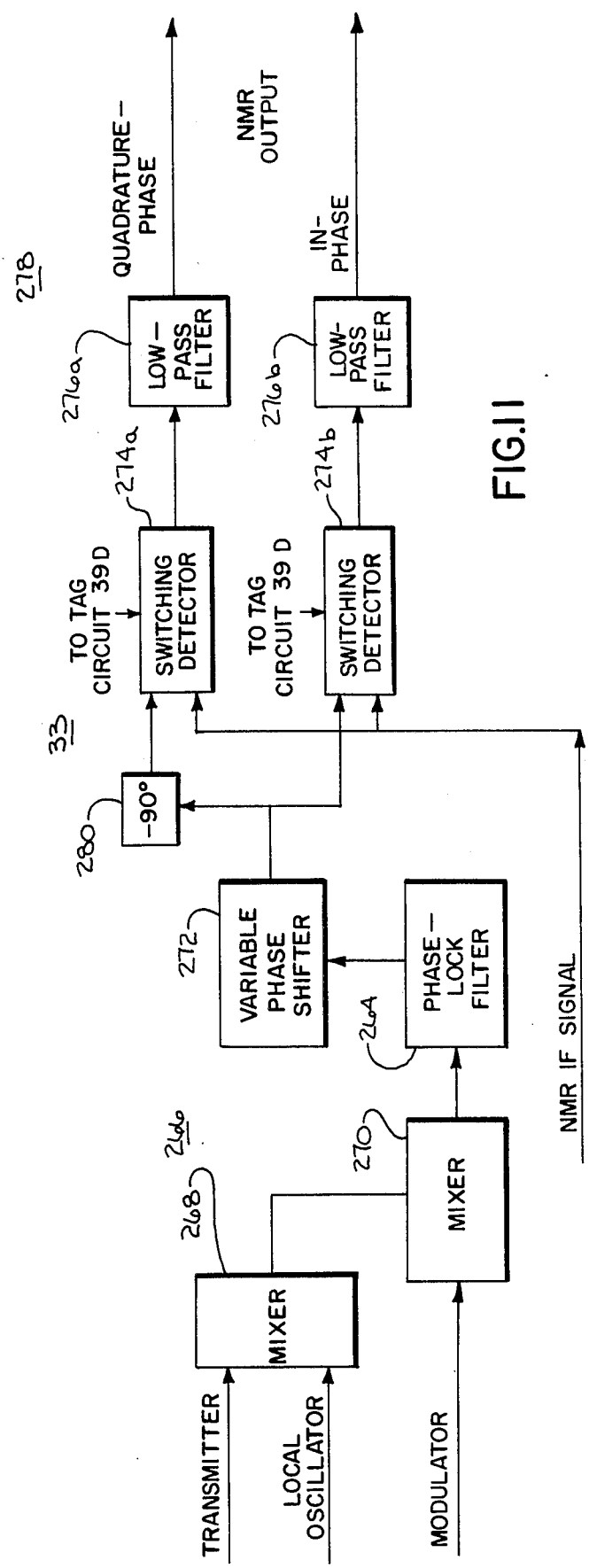

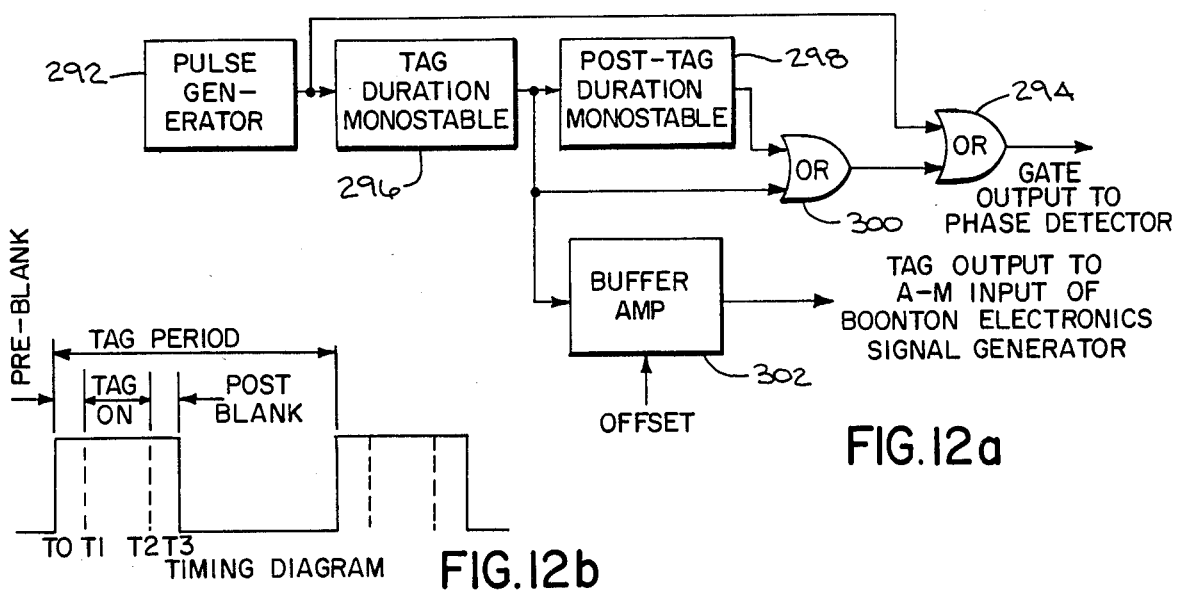
FIG.12a
FIG.12b
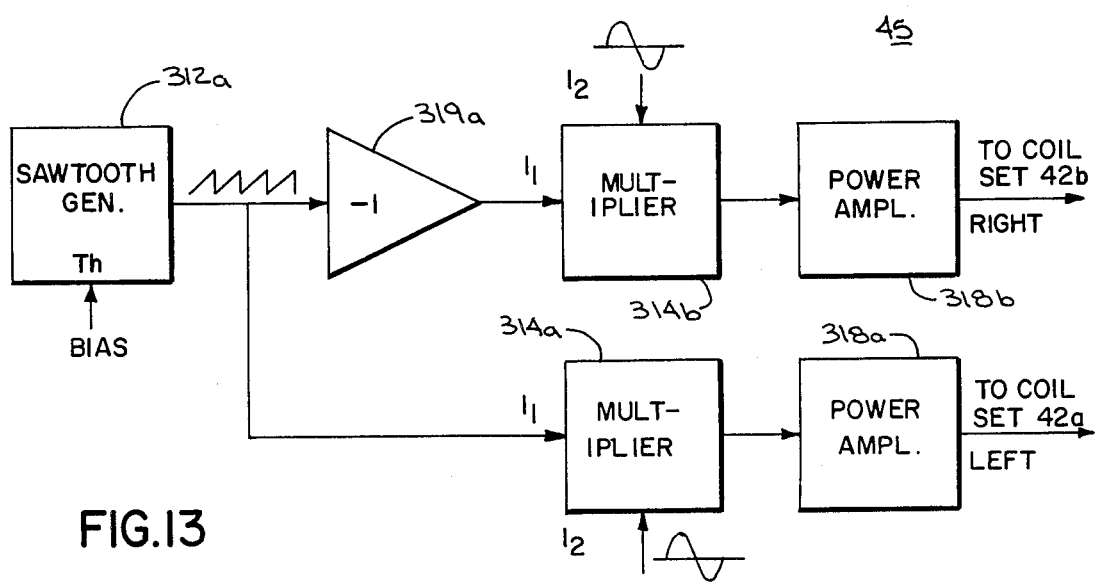
FIG.13
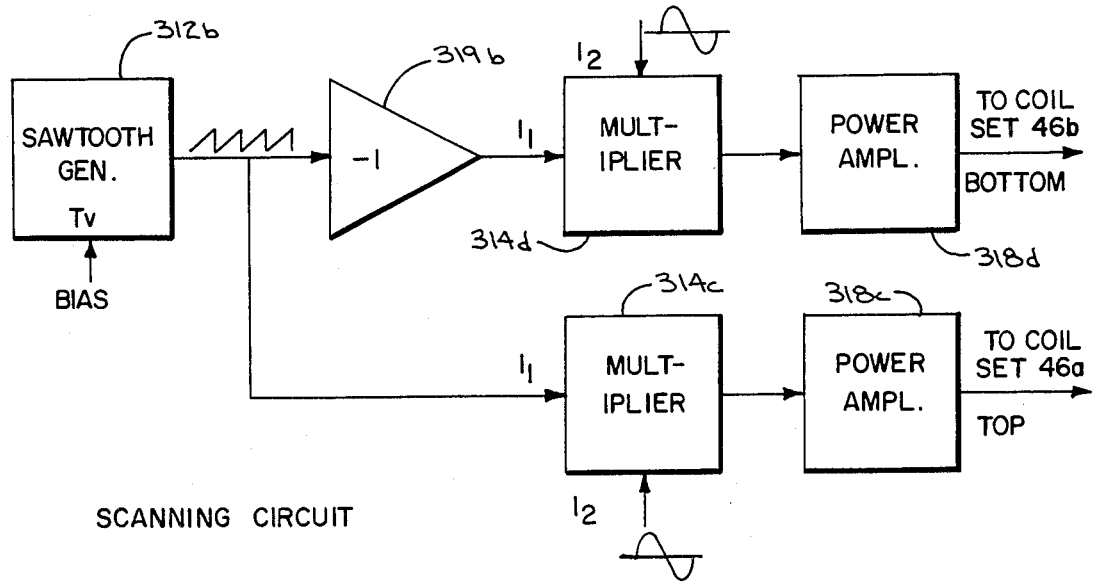

NUCLEAR MAGNETIC RESONANCE BLOOD FLOWMETER

FIELD OF THE INVENTION

The field of this invention is nuclear magnetic resonance blood flowmeters for non-invasive measurement of blood flow in limb members and more particularly a nuclear magnetic limb blood flow meter which enables two dimensional imaging of the blood flow through the limb.

BACKGROUND OF THE INVENTION

Accurate, non-invasive blood flow measurement has long been a goal of medical researchers. Non-invasive measurement of blood flow in the limb and especially the leg where most vascular diseases occur would facilitate early detection of such diseases. Such early detection would enable diagnosis and treatment of the disease before limb amputation would be necessary. As detailed in the paper "The NMR Blood Flowmeter, Theory and History" by Joseph H. Battocletti, Richard E. Halbach, Sergio X. Salles-Cunha, and Anthony Sances, Jr., published in the July/August 1981 issue of Medical Physics, Vol. 8(4) at pages 435-443, following the discovery of the phenomenon of nuclear magnetic resonance, scientists began experimenting to determine if liquid flow could be measured non-invasively using the principles of nuclear magnetic resonance. It was soon discovered that the nuclear magnetic response signal induced in a moving, paramagnetic fluid was low when fluid velocity was low due to saturation in the detector but the NMR signal magnitude increase in response to an increase in fluid velocity as a consequence of magnetized nuclei entering the detector from upstream of the saturation region.

Later advances in the field of nuclear magnetic resonance fluid measurement included the discovery that fluid flow could be detected by magnetically "tagging" a bolus of the fluid. By physically locating a small magnetic coil, commonly referred to as a "tag" coil ahead of the NMR transmitter and receiver coils such that the tag coil, when energized with a fixed radio frequency signal produced a field orthogonal to the polarizing field, a bolus of fluid could be given a magnetic orientation different from an adjacent bolus. When this tagged bolus reached the receiver coil, a brief unidirectional pulse would be induced in the receiver coil. From a knowledge of the time that had elapsed between tagging of the bolus and detection of the tagged bolus at the coil receiver and from a knowledge of the distance between the tag coil and the receiver coil, fluid velocity could be determined. Examples of nuclear magnetic resonance fluid flowmeters for measuring fluid flow in this manner are found in U.S. Pat. Nos. 3,419,793, 3,419,795, 3,551,794 and 3,473,108.

Nuclear magnetic resonance fluid flow measuring methods have been employed to construct experimental blood flowmeters for non-invasive measurement of blood flow. The structure of a typical, present day experimental nuclear magnetic resonant blood flowmeter is described in the paper "A Nuclear Magnetic Resonance Non-invasive Leg Blood Flow-Meter" by J. H. Battocletti, R. E. Halbach, A. Sances, Jr. and F. J. Antonich published in the Conference record of the IEEE 1981 Conference "Frontiers of Engineering Health Care," Houston, Tex., Sept. 19-21, 1981 at pages 145-147. Generally, a NMR blood flowmeter includes a pair of polarizing magnets which serve to polarize the blood flow flowing in a bodily member, such as a limb which is disposed within a lumen located between the magnet poles. A receiver coil and a transmitter coil, typically arranged so that the field direction of the coils is orthogonal to each other, are carried by the lumen so as to be located between poles of the polarizing magnet. Located on the lumen upstream of the detector and transmitter coils is a tag coil which is oriented such that when energized with a fixed radio frequency signal, the tag coil generates a magnetic field orthogonal to the polarizing field so as to tag or demagnetize a bolus of blood. When this tagged bolus reaches the receiver coil, the output signal of a receiver coupled to the receiver coil will deviate. The deviation in the receiver output signal is detected by a detector. By measuring the time between deviations of the receiver output signal and by knowing the distance between the tagging coil and the detector, blood flow can then be calculated.

Further research in the field of non-invasive limb blood flow measurement using the principle of nuclear magnetic resonance has led to the development of a nuclear magnetic resonance blood flowmeter which enables ranging or focusing of the nuclear magnetic resonance response within a single plane. Thus, the limb bloodflow can be "imaged" in a single plane in a manner similar to the way in which X-rays are now imaged. An experimental nuclear magnetic resonance blood flowmeter capable of one dimensional imaging or ranging has been described in the paper "Ranging for Individual Artery Flow in the Nuclear Magnetic Resonance Flow Meter" by Richard E. Halbach, Joseph A. Battocletti, Anthony Sances, Robert Bowman, and Vsevolod Kudravcev published in the conference record of the IEEE 1981 Conference "Frontiers of Engineering in Health Care", Washington, D.C., Sept. 28-29, 1980 at pages 356-359. The experimental blood flowmeter described in the Halbach et al. paper is similar to that described previously except that it also includes a pair of scanning or ranging coil sets. The coils are each located on opposite sides of the lumen or limb receiving cavity so as to be orthogonal to the polarizing magnets of the nuclear magnetic resonance blood flowmeter. When the coils of each of the pair is energized with a current opposite in polarity to the current in the other of the scanning coils, each scanning coil generates a magnetic field opposite in polarity to the field generated by other of the pair of scanning coils. These opposing fields tend to cancel the nuclear magnetic resonance response everywhere except in a null plane where the fields of the scanning coils tend to cancel themselves. By varying the ratio of the current in the scanning coils, the null plane of the scanning coils, that is, the plane of the nuclear magnetic response can be shifted across the lumen to allow imaging of the limb in one dimension.

While the scanning type nuclear magnetic resonance blood flowmeter, such as described in the Halbach et al. paper, accomplishes one dimensional scanning or ranging of the nuclear magnetic resonance response induced in the blood, thereby enabling blood flow measurement within a single artery to the exclusion of others, one dimensional ranging or imaging-type nuclear magnetic resonance blood flowmeters do not provide any indication of arterial or venous blood flow along a particular base line. To accomplish non-invasive blood flow measurement within an artery or vein along a certain base line would require imaging in two dimensions, something that has not heretofore been accomplished by prior art nuclear magnetic resonance blood flowmeters.

In order for present day experimental nuclear magnetic resonance blood flowmeters, such as the type disclosed in the Battocletti et al. paper or the ranging type nuclear magnetic resonance blood flowmeter described in the Halbach et al. paper to accomplish accurate detection of blood flow, the magnetic field of the polarizing magnet must be uniform and remain relatively constant. To provide for coarse adjustment of the uniformity of the magnetic field generated by the polarizing magnets, mechanical shims, taking the form of rectangular steel strips, are placed on the pole faces. Relatively fine adjustment of the magnetic field is accomplished by electromagnetic coils located around the magnet poles. The electromagnetic coils are energized by a closed loop control circuit responsive to the polarizing magnet flux. In the past, Hall effect sensors have been utilized as the flux sensing element for the closed loop control circuit energizing the pole face electromagnetic coils. However, such Hall effect sensors are typically temperature sensitive so that the flux measurement provided thereby tends to vary with the ambient temperature of the Hall effect sensor. Thus, as the magnet temperature rises, the Hall effect sensor temperature rises and the magnetic flux sensed by the Hall effect sensor will thus vary, resulting in undesirable variations in the magnetic flux generated by the electromagnetic coils. This ultimately causes an undesirable variation in the polarizing magnet flux.

BRIEF SUMMARY OF THE INVENTION

The present invention concerns an improved nuclear magnetic resonance blood flowmeter which accomplishes two dimensional imaging of blood flow so as to enable noninvasive arterial or venous blood flow measurement above a particular baseline. The blood flowmeter of the present invention includes a unique Hall effect sensor stabilizer circuit which maintains the temperature of the Hall effect sensor constant to assure precise measurement of the polarizing flux density which enables the polarizing field to remain constant. To enable venous blood flow to be measured accurately by the active tag method without interference from the tagging signal, a tag select circuit is provided for disabling the blood flowmeter prior to, during and just after generation of a tag signal.

The blood flowmeter of the present invention is configured of a pair of polarizing magnets, each disposed on opposite sides of a limb receiving lumen which supports the limb within field of the polarizing magnet. The field of the polarizing magnets is kept constant by a field controller circuit which includes a pair of electromagnetic coils which are each located around each of the polarizing magnets. A regulator circuit energizes the electromagnetic coils in accordance with the polarizing field flux as sensed by a Hall effect sensor which is thermally stabilized by a stabilizer circuit. A nuclear magnetic resonance response is induced in the magnetically polarized blood molecules by a transmitter whose transmitter coil is orthogonally oriented to the coil of the detector which detects the induced nuclear magnetic response. The detector output signal, which varies in accordance with the induced NMR response thus provides a very good indication of arterial blood flow, due to the self-tagging effect of the polarizing field. Venous blood flow can also be determined from the detector output signal following active tagging of the blood by way of a tag circuit which energizes a tag coil located within the field of the polarizing magnet upstream of the transmitter and detector coils. The tag circuit of the NMR blood flowmeter includes a tag select circuit for disabling the detector during intervals while the tag coil is energized to reduce interference with the transmitter signal.

Two dimensional scanning of the limb to enable measurement of blood flow through a single artery or vein above a selected baseline is accomplished through the use of two sets of scanning coils, the coils of each set being on opposite sides of the lumen and the scanning coils of each set being at a preselected angle, typically 90°, from each of the scanning coils of the other set. A control circuit energizes the coils of each scanning coil set with currents so that the coils of each set generate opposing magnetic fields. The opposing fields of each set of scanning coils tend to cancel the NMR response everywhere except along a single null plane along which the opposing fields of the scanning coils of each set cancel each other. Thus, the NMR response exists only along a single line created by the intersection of the two null planes which are each generated by a separate one of the two pairs of scanning coils. By varying the current in the opposing coils of each scanning coil pair, the control circuit can effectively shift the line of intersection of the null planes, thereby shifting the line of induced NMR response to allow ranging or scanning of the limb in two dimensions.

It is a general object of the present invention to provide an improved nuclear magnetic resonance blood flow-meter for non-invasive blood flow measurement in a human limb and which advantageously enables two dimensional scanning or ranging of the limb to facilitate blood flow measurement within a selected artery or vein above a particular base line. This is accomplished in the present invention by the addition of two pairs of scanning or ranging coils disposed within a nuclear magnetic resonance blood flowmeter so that the coils of each set are located on opposite sides of the limb receiving lumen so as to be perpendicular to each of the coils of the other set of scanning coils. A control circuit energizes each of scanning coils of each set with a current so as to generate a magnetic field opposite in polarity to the field in the other scanning coil of the same set. By varying the magnitude of current in the coils of each of the scanning coil sets, each of the null planes produced by each pair of scanning coil sets may be shifted through the limb so that the induced nuclear magnetic resonance response, which appears only at the intersection of the two null planes, can be shifted through the limb.

It is another general object of the present invention to provide an improved nuclear magnetic resonant blood flowmeter for accurately measuring blood flow non-invasively. This is accomplished in the present invention by an improved nuclear magnetic resonance blood flowmeter which includes a field stabilizing circuit for maintaining the flux generated by the polarizing magnets of the blood flowmeter substantially constant. The field stabilizing circuit includes a temperature compensated Hall effect sensor for accurately measuring the polarizing magnet flux notwithstanding magnet temperature variation. A control circuit controls the energization of a pair of electromagnets each disposed around the pole of each polarizing magnet in accordance with the flux sensed by the flux sensor so that the flux of the polarizing magnet is maintained substantially constant by the field stabilizing circuit.

BRIEF DESCRIPTION OF THE DRAWINGS

The features of the present invention believed to be novel are set forth with particularity in the appended claims. The invention itself, however, both as to organization and method of operation, together with further objects and advantages thereof may best be understood by reference in the following description taken in conjunction with the accompanying drawings in which:

FIG. 10 is an electrical block diagram of the receiver circuit of the NMR blood flowmeter of FIG. 5;

FIG. 11 is an electrical block diagram of the triple mixer and synchronous phase detector of the NMR blood flowmeter of FIG. 5;

FIG. 12a is an electrical block diagram of the tag select circuit of the NMR blood flowmeter of FIG. 5;

FIG. 12b is a timing diagram for the tag select circuit of FIG. 12a;

FIG. 13 is an electrical block diagram of the preferred embodiment of the scanner control circuit of the NMR blood flowmeter of FIG. 5;

DETAILED DESCRIPTION OF THE PREFERRED EMBODIMENT

Figure 1:
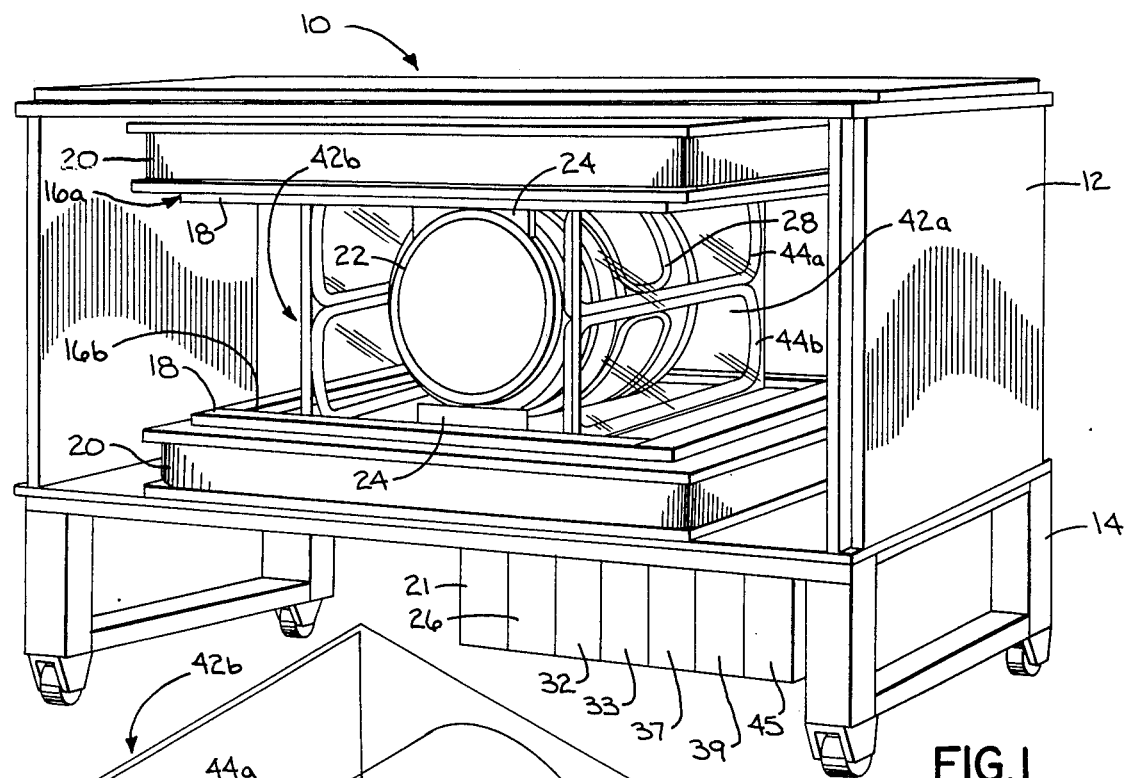
FIG. 1 is a perspective view of an improved nuclear magnetic resonant blood flow meter.

Before proceeding to describe the nuclear magnetic resonance blood flowmeter of the present invention, a brief understanding of the phenomenon of nuclear magnetic resonance may be helpful. Each atom of a molecule, such as a water molecule within human blood, is comprised of an atomic nucleus and electrons which orbit about the nucleus. The atomic nuclei consists of positively charged atomic particles known as protons and neutrally charged atomic particles known as neutrons. Each of the neutrons and protons rotates about its own axis. When the atomic nuclei is comprised of an even number of protons and neutrons, the spin of the protons and neutrons tend to cancel each other. If, however, the atomic nucleus possesses an odd number of protons and neutrons, such as the case of the hydrogen atom of a water molecule, then the nucleus possesses a net atomic spin. As a result of the net atomic spin, the nuclei which is positively charged, acts as a spinning magnet having a north and south pole.

When a molecule having a spinning nuclei, such as the hydrogen atoms of a water molecule, is subjected to a very strong magnetic field, the spinning nuclei align themselves either parallel or anti-parallel to the direction of the field and will precess about an axis parallel to the field direction at a frequency $f_o$ referred to as the Larmor frequency. As the atomic nuclei align themselves to the direction of the polarizing magnetic field, more align themselves parallel to the field direction than align themselves anti-parallel to the polarizing field direction. Therefore, a net magnetization is obtained. However, if the nuclei are also subjected to an alternating magnetic field having a direction perpendicular to the direction of the polarizing field, then some of the atomic nuclei aligned parallel to the direction of the polarizing field will flip and align themselves anti-parallel to the polarizing field direction. To obtain the necessary energy to complete such a change in orientation, the nuclei absorb energy from the magnetic field. The total amount of energy absorbed from the alternating magnetic field, which is usually generated by a radio frequency transmitter, is greatest when the frequency of the alternating magnetic field is resonant with the Larmor frequency, which for blood is typically given by the relationship $f_o = 4.2577 \times 10^{+7} B_o$ Hz, where $B_o$ is the strength of the polarizing field in telsa. This phenomenon of equalization of spin populations is known as "saturation", a knowledge of which is necessary to understand the principles of flow detection.

The above described phenomenon of nuclear magnetic resonance can be used to measure both arterial and venous blood flow. Arterial blood flow is usually measured using a "self-tag" technique. In the artery, blood flow tends to be pulsatile, with the greater flow rate occurring during intervals of systolic flow and the lower flow rate occurring during intervals of diastolic flow. When the blood molecules within an artery are subjected to both a polarizing magnetic field and an alternating magnetic field at or near the Larmor frequency then, a "saturation" notch occurs in the region of the detector coil. During periods of diastolic flow, blood residing in the detector coil region becomes saturated, causing a low NMR response. However, during periods of systolic flow, the NMR response increases due to the passage of magnetized nuclei into the detector region. By detecting this alternation of NMR response, arterial blood flow can be easily measured. Alternatively, an elevated NMR response is obtained from moving blood compared with blood at rest. This NMR response is porportional to volumetric blood flow rate.

To measure venous blood flow, a bolus of blood in the vein is actively "tagged" or "demagnetized" upstream of the transmitter coil which produces the alternating frequency magnetic field, and the detector coil which is coupled to the detector which detects the moving magnetized nuclei. When the tagged bolus reaches the transmitter and detector coils, the detected nuclear magnetic response deviates so that by knowing the distance between the tagging station and the detector station, and by knowing the time required for the tag nuclei to pass from the tagging station to the detector station, the velocity of venous blood flow can be measured. Together with a measurement of the amplitude of the response, volumetric blood flow rate can be determined.

Figure 1A:
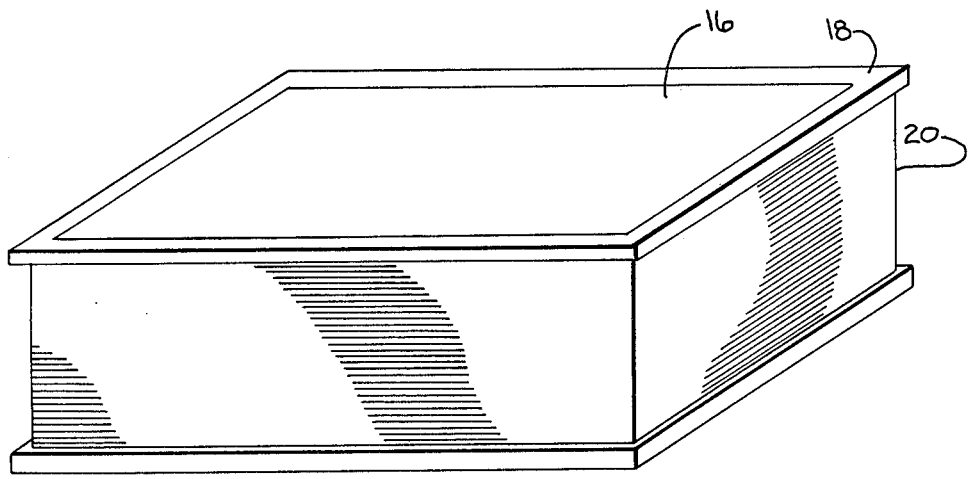
FIG. 1a is a perspective view of a portion of the blood flowmeter of FIG. 1 illustrating the details of one of the polarizing magnets.

Referring now to the figures, FIG. 1 illustrates an improved apparatus 10 for non-invasively measuring blood flow using the principal of nuclear magnetic resonance. Nuclear magnetic resonance blood flowmeter 10 comprises a rectangular steel shell 12 which is supported by a rollable cart 14. Within shell 12 is a pair of oppositely poled polarizing magnets 16a and 16b which are each typically located on the top and bottom interior surfaces, respectively, of the shell. In practice, each of magnets 16a and 16b is comprised of a magnetic pole piece fabricated from ceramic permanent magnet material, such as ceramic Type 5 or Type 8. Alternatively, rare-earth magnet material may be used. To insure coarse homogeneity of the field produced by magnets 16a and 16b, a magnetic shim 18, consisting of a steel ring, is placed on the pole face of each magnets 16a and 16b. Referring now to FIG. 1A which is a perspective view of magnet 16a, very fine adjustment of the magnetic field produced by each magnet, such as magnet 16a for example is achieved by an electromagnetic coil 20 located on the surface of the pole face of each of magnets 16a and 16b so as to be circumscribed by magnetic shim 18. As will become better understood hereinafter, each of electromagnetic coils 20 is energized by a field controller circuit 21 (described in greater detail with respect to FIGS. 6, 7 and 8) in accordance with the flux of magnets 16a and 16b. In practice, circuit 21 is packaged in an enclosure mounted directly to cart 14 underlying shell 12.

Located within shell 12 is a magnetically permeable cylinder or lumen 22 which is held between magnets 16a and 16b by chocks 24. Lumen 22, is typically manufactured from a PVC pipe having a 20.3 centimeter internal diameter and 0.5 centimeter thick walls. The dimensions of the lumen are chosen to enable the lumen to support a human limb therein so that the water molecules of blood flowing through the limb are magnetized by permanent magnets 16a and 16b.

Figure 2:
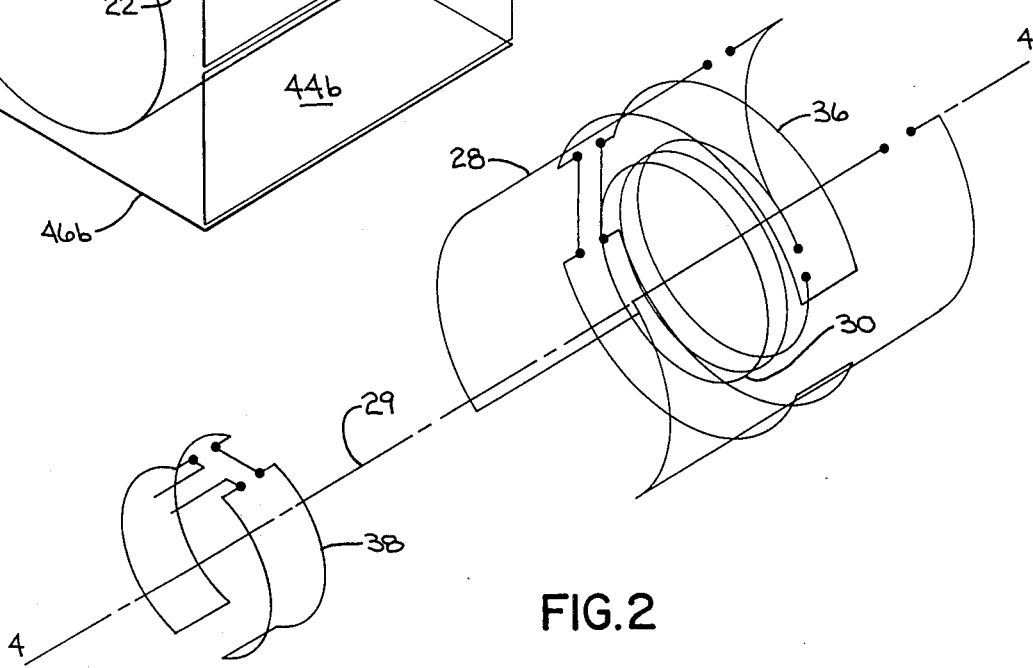
FIG. 2 is a perspective view of a portion of the blood flowmeter of FIG. 1 illustrating the arrangement of the transmitter, receiver, modulator, and tag coils.

A nuclear magnetic resonance response is induced in the water molecules of the blood flowing through the limb by a transmitter 26 (described in greater detail with respect to FIG. 9) whose output signal is supplied to a transmitter coil 28 which circumscribes lumen 22. Transmitter 26 is packaged within an enclosure physically mounted to cart 14 beneath shell 12 so as to be adjacent to field controller circuit 21. Referring now to FIG. 2 which is a simplified perspective view of the nuclear magnetic resonance blood flowmeter with the shell, the polarizing magnets and the lumen not shown, transmitter coil 28 is wound so that the direction of the field produced thereby is perpendicular to the lumen axis represented by the dash-dotted line 29. The nuclear magnetic resonance induced by the field of the transmitter coil is detected by a receiver coil 30 which is coupled to a receiver 32 which, as illustrated in FIG. 1, is carried in an enclosure mounted to cart 14 beneath shell 12 so as to be adjacent to transmitter 26.

As will become better understood hereainfter, receiver 32 (which is described in greater detail in FIG. 10), is operative to generate an intermediate frequency signal whose amplitude deviates in response to a flow signal induced in receiver coil 30. A detector 33 (described in greater detail in FIG. 11) is physically disposed in an enclosure mounted to cart 14 beneath shell 12 so as to be adjacent to receiver 32 and is operative to detect the amplitude deviation of the receiver intermediate frequency output signal. The detector output signal, which is indicative of induced NMR response, will be seen as being responsive to blood flow.

Returning to FIG. 2, the receiver coil 30 is wound about the lumen (not shown) so that the axis of the field induced in receiver coil 30 is perpendicular to the axis of the field produced by transmitter coil 28. By cross coupling the transmitter and receiver coils, that is, by orienting the transmitter and receiver coils so that their respective fields are orthogonal to each other, the mutual inductance of the coils is thus reduced and a high degree of isolation between the coils is achieved.

In addition to the transmitter and receiver coils being wrapped about the lumen (not shown), a modulation coil 36 and a tag coil 38 are also wrapped about the lumen, with the tag coil 38 being located upstream of the transmitter, receiver, and modulation coils. Modulation coil 36 and tag coil 38 are each wound so that the field generated thereby is perpendicular to the lumen axis 29. As will become better understood hereinafter by reference to FIG. 5, modulation coil 36 is energized from a modulator 37 physically disposed within an enclosure mounted to cart 14 beneath shell 12 so as to be adjacent to detector 33, with an approximately 8 kilohertz audio frequency field to superimpose a magnetic field, hereinafter referred to as the $B_m$ field on $B_o$ the magnetic field produced by magnets 16a and 16b. With the $B_o$ field modulated by the $B_m$ field, the receiver 32 can be advantageously tuned to a side band of the transmitter frequency to further reduce the interference therebetween.

The tag coil 38 is energized with a radio frequency signal at periodic intervals by a tag circuit 39 (described in greater detail in FIG. 5), the tag circuit 39 being physically disposed within an enclosure mounted to cart 14 beneath shell 12 so as to be adjacent to modulator 37. When energized with a radio frequency signal from tag circuit 39, tag coil 38 generates a magnetic field orthogonal to the $B_o$ field to impart a particular magnetic orientation to a bolus of blood at a particular instant in time.

Figure 4:
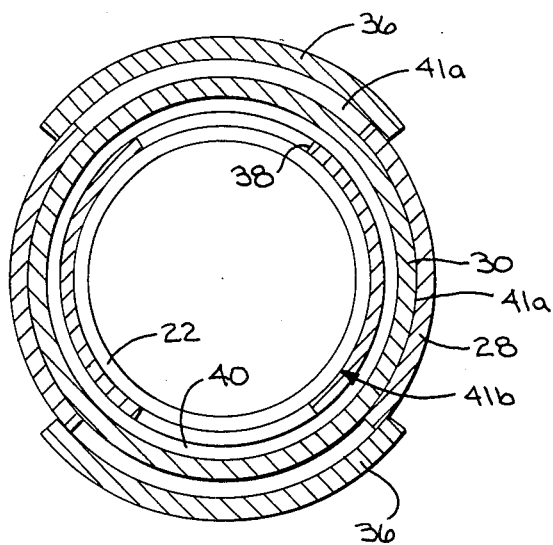
FIG. 4 is an end view taken along lines 4—4 of FIG. 2.

Referring to FIG. 4 which is a cross sectional view of the lumen, it can be seen that modulator coil 36, transmitter coil 28, receiver coil 30 and tag coil 38 are concentrically wrapped about lumen 22, with the modulator coil being furthest from the lumen and the tag coil being closest to the lumen. A spacer 40 separates the tag coil 38 from the receiver coil 30 and a first rake or Faraday Shield 41a separates the receiver coil 30 from the transmitter coil 28. The Faraday Shield helps reduce the coupling between the transmitter and receiver coils. A second rake shield 41b separates the receiver coil 36 from the lumen volume and is located on the outside surface of the lumen 22.

Returning now to FIG. 1, each pair of scanning coil sets 42a and 42b is located on opposite sides of lumen 22 so that the coil sets are parallel and spaced apart from each other. Each scanning coil set comprises a pair of coils 44a and 44b which are stacked on top of each other. When each of the coils of each set are energized with opposing polarity audio frequency signals from a scanner circuit 45 (described in FIG. 14) which is disposed in an enclosure mounted to cart 14 beneath shell 12 as to be adjacent to tag circuit 37, the coils generate opposing magnetic fields which are oriented parallel to the magnetic field produced by magnets 16a and 16b. These opposing fields tend to cancel themselves along a null plane parallel to the field direction of the coils.

Figure 3:
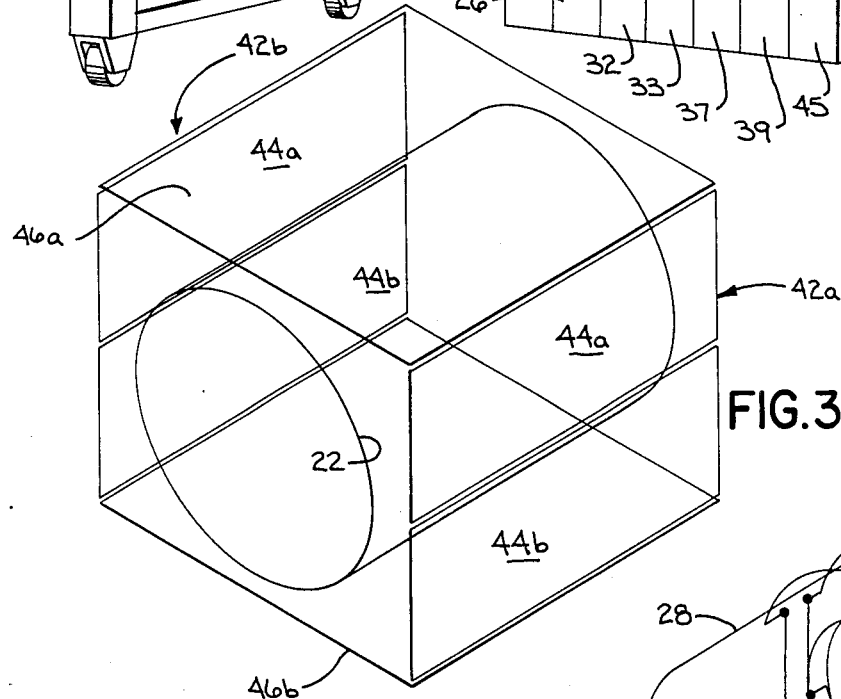
FIG. 3 is a perspective view of a portion of the blood flowmeter of FIG. 1 illustrating the arrangement of the scanning coils.

Turning now to FIG. 3, a second pair of scanning coil sets 46a and 46b are located on either side of lumen 22 so as to be in spaced apart relationship with each other and so as to be at a preselected angle with the coils of one of scanning coil sets 42a and 42b. In practice, each of scanning coils 46a and 46b is perpendicular to each of scanning coil sets 44a and 44b. Scanning coils 46a and 46b are also energized with opposing polarity audio frequency signals from scanner circuit 45 to generate opposing magnetic fields. The opposing fields generated by scanning coils 46a and 46b tend to cancel themselves along the null plane orthogonal to the field direction of scanning coils 46a and 46b and orthogonal to the null plane produced by the opposing fields of scanning coil sets 42a and 42b. The current in each of the scanning coils of 44a and 44b of scanning coil sets 42a and 42b and the current in scanning coils 46a and 46b, is varied by scanner circuit 45 in a manner described in greater detail hereinafter so that the null planes generated by each of the pair of scanning coils can be shifted across the lumen to shift the position of the intersection line of the null planes.

Figure 5:
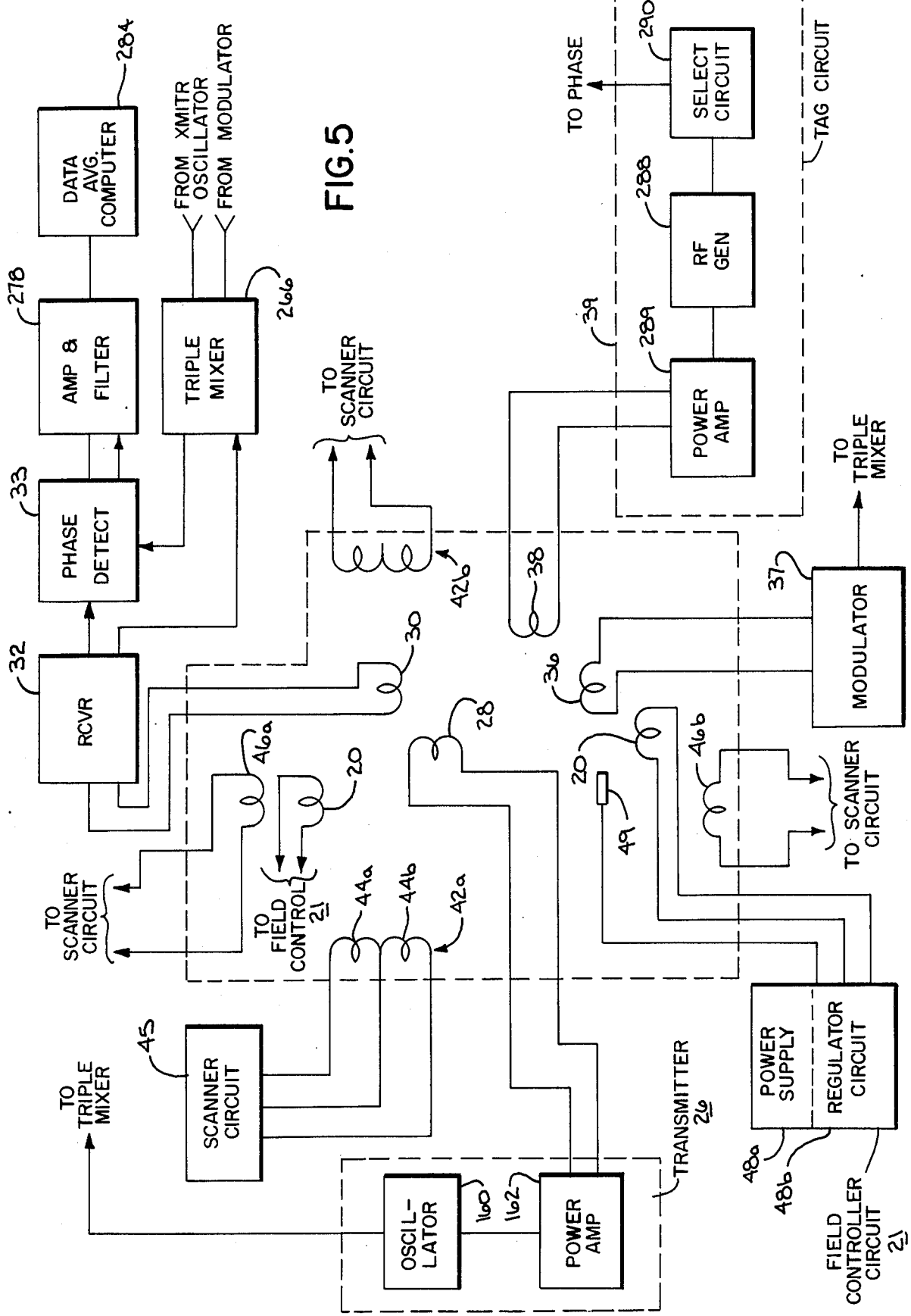
FIG. 5 is an electrical block diagram of the nuclear magnetic resonance blood flowmeter of FIG. 1.

Having now provided a general physical description of the nuclear magnetic resonance blood flowmeter of the present invention, a better understanding of the electrical circuitry associated with each of the previously described coils for accomplishing non-invasive blood flow measurement may now be gained by reference to FIG. 5 which is a block electrical diagram of the nuclear magnetic resonant blood flowmeter of the present invention. As previously described, each of electromagnetic coils 20, which are wrapped around the separate pair of magnets 16a and 16b, is energized by a field controller circuit 21 in accordance with the polarizing magnetic flux. The field controller circuit 21, described generally with respect to FIG. 1, includes a DC power supply 48a described in greater detail with respect to FIG. 6 and a field regulator circuit 48b described in greater detail with respect to FIG. 7 for regulating the amount of DC voltage supplied from the power supply 48a to each of coils 20 in accordance with the polarizing flux measured by flux sensor 49 which is described with respect to FIG. 8.

POWER SUPPLY 44a

Figure 6:
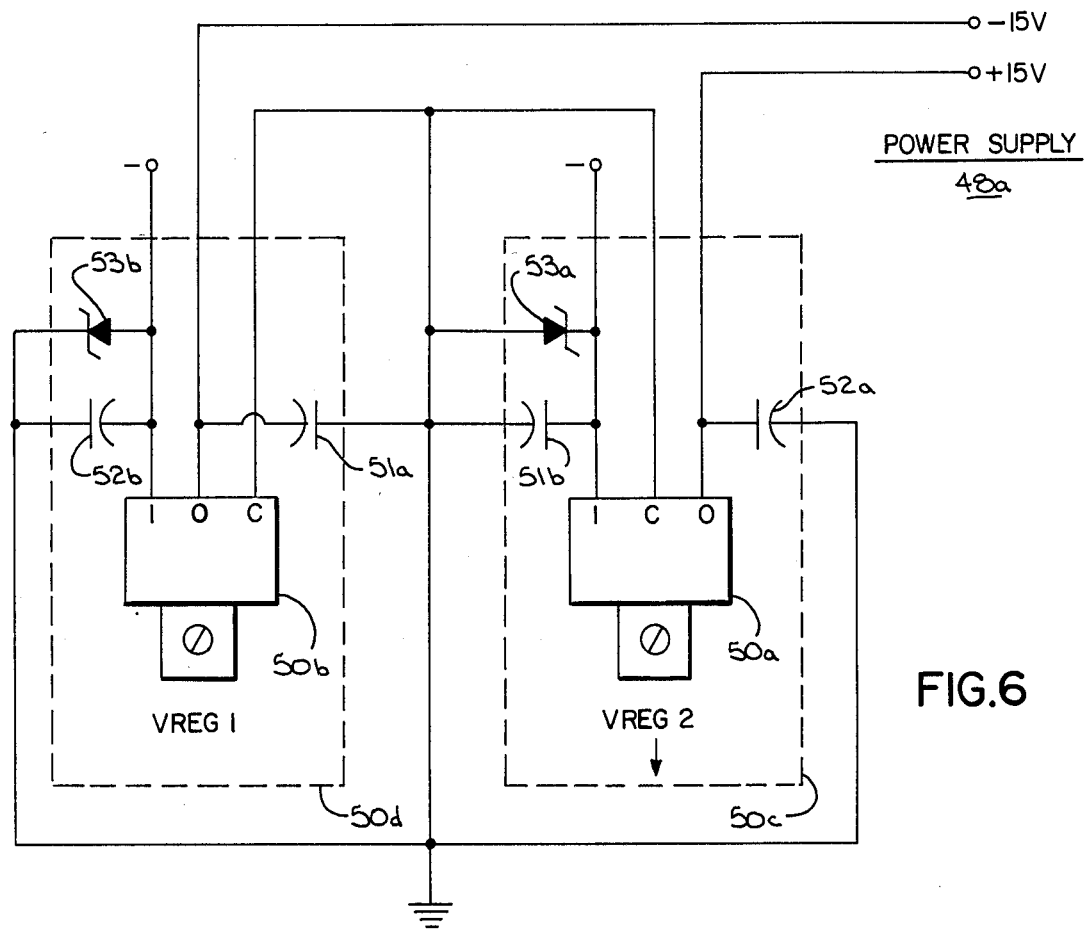
FIG. 6 is a part schematic, part block diagram of the power supply of the field controller circuit of the nuclear magnetic resonance flowmeter illustrated in FIG. 5.

The details of power supply circuit 48a are illustrated in FIG. 6. At the heart of the power supply circuit is a pair of voltage regulators 50a and 50b which are each mounted on separate heat sinks 50c and 50d, respectively. Voltage regulators 50a and 50b, comprise a model UA 7815 and a model UA 7915 voltage regulator, respectively, as manufactured by Fairchild Semiconductor, Inc. The regulators 50a and 50b have their respective input terminals I coupled to the positive (+) and negative (−) terminals, respectively, of an unregulated DC voltage supply (not shown). The common terminal C of regulator 50a is connected to the junction of the output terminal O of regulator 50b and circuit ground. With the regulators 50a and 50b connected in this fashion, when an unregulated DC voltage of approximately 24 or more volts is applied between the respective input terminal I of regulators 50a and 50b, a +15 volt DC voltage appears between the output terminal O of regulators 50a and circuit ground and a −15 volt DC output voltage appears between the common terminal C of regulator 50b and circuit ground. The output terminal O of regulator 50a and the common terminal C of regulator 50b are hereinafter designated as the +15 V and −15 V terminals, respectively of power supply 48a.

Capacitances 51b and 52b are connected from the input terminals I of regulator 50a and 50b, respectively to ground. Capacitances 51a and 52a are connected between the +15 V and 15 V terminals and ground, respectively. Capacitances 51a and 51b and 52a and 52b serve in combination to filter the +15 and the −15 DC voltages produced by the power supply 48a, and to keep the regulators 50a and 50b from unwanted oscillations. Protection against excessive incoming voltage is provided by a first Zener diode 53a having its cathode connected to the input I of regulator 50a and its anode connected to circuit ground and a second Zener diode 53b having its cathode connected to circuit ground and its anode connected to the input I of regulator 50b.

REGULATOR CIRCUIT 48b AND FLUX SENSOR 49

Figure 8:
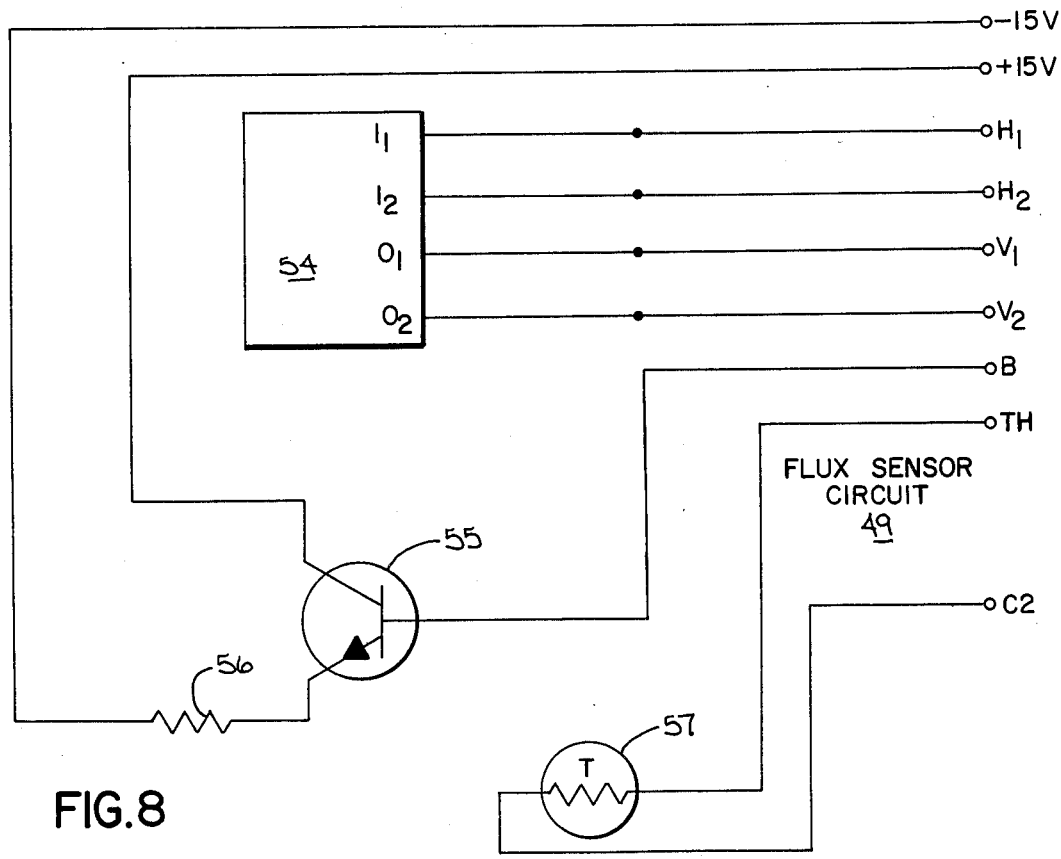
FIG. 8 is a part block, part schematic diagram of the Hall effect sensor circuit comprising a part of blood flowmeter of FIG. 5.

The details of the field regulator circuit 48b will be described in FIG. 7 in connection with the flux sensor circuit 49 illustrated in FIG. 8. In order to better understand the details of the field regulator circuit 48b of FIG. 7, it will be useful to first describe the flux sensor circuit 49 of FIG. 8. Referring now to FIG. 8, flux sensor circuit 49 comprises a Hall effect probe 54 which typically takes the form of a Model HR72 Hall effect probe manufactured by Ohio Semitronics, Inc., Columbus, Ohio. When Hall effect probe 54 is supplied with an input current at its input terminals $I_1$ and $I_2$, which are each coupled to terminals $H_1$ and $H_2$ of the field regulator circuit 48b, the Hall effect probe 54 produces a d.c. voltage at its output terminals $O_1$ and $O_2$ which varies in accordance with the flux penetrating or permeating the probe. The output terminals $O_1$ and $O_2$ are coupled to field controller circuit 48b terminals $V_1$ and $V_2$. Since the output voltage of Hall effect probe 54 tends to decrease as the ambient temperature rises, either the input current to the Hall effect probe 54 must be precisely controlled in accordance with temperature or the ambient temperature must be measured so that changes can be accounted for. The Hall effect probe 54 is not only thermally stabilized, but the input current provided to the Hall probe 54 is sensed by circuit 48b in a manner described hereinafter to assure that the output voltage of the Hall effect probe 54 accurately reflects the flux permeating the probe.

To thermally stabilize Hall effect probe 54, the Hall effect probe is mounted in thermal contact with a power transistor 55 whose collector-to-emitter portion is coupled in series with a 10 ohm resistance 56 across the +15 V and common terminals of power supply 48a. As will become better understood following the description of field regulator circuit 48b of FIG. 7, transistor 55 is coupled at its base to terminal B of the field regulator circuit 48b and is supplied from the field regulator circuit with a voltage to render the transistor conductive in its linear conduction range in accordance with the resistance of a thermistor 57. The thermistor is in physical contact with Hall effect probe 54 and is electrically coupled between the common terminal C of power supply 48a (FIG. 6) and the field regulator circuit terminal TH. When the transistor 55 is rendered conductive, the transistor dissipates heat which in turn heats the Hall effect probe 54 and thermistor 57.

Figure 7:
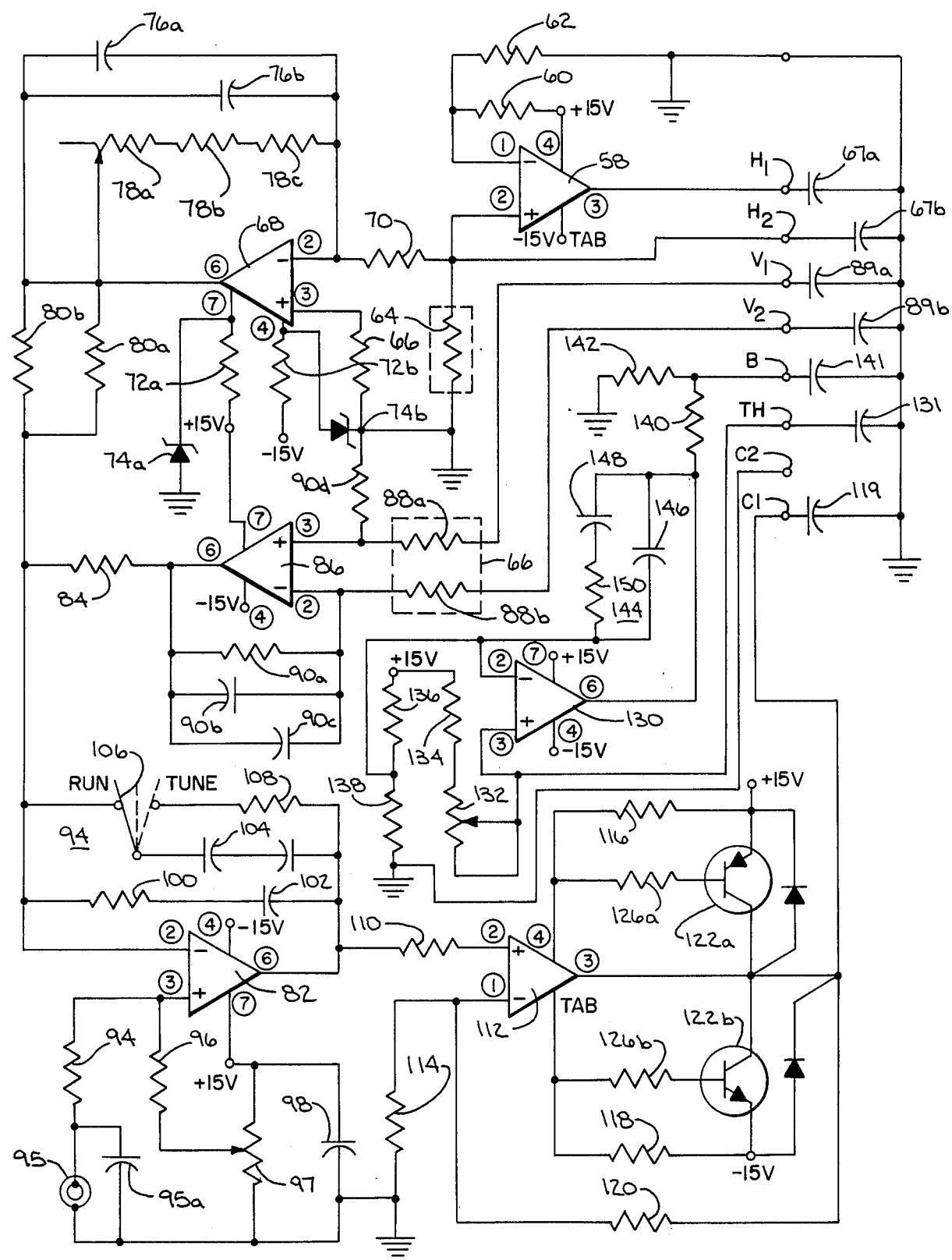
FIG. 7 is an electrical schematic diagram of the field regulator circuit of the nuclear magnetic resonance blood flowmeter illustrated in FIG. 5.

The details of the field regulator circuit 48b are illustrated schematically in FIG. 7. Field controller 48b includes a first operational amplifier 58 which is coupled at its positive and negative power input terminals (pins 7 and 4) to the +15 V and −15 V terminals, respectively of the power supply 48a. The invert input (pin 3) of the operational amplifier 58 is coupled via a resistance 60 to the +15 V terminal of the power supply 44a and is also coupled via a resistance 62 to circuit ground. Operational amplifier 58 has its non invert input (pin 2) coupled to one terminal of a resistance 64 whose other terminal is coupled to circuit ground. Resistance 64 is mounted on a heat sink 66 which typically takes the form of a copper plate in thermal contact with but electrically insulated from resistance 64 so that the heat produced by the resistance is dissipated by the heat sink. When supplied with a substantially constant voltage at its invert input from the power supply 48a, the operational amplifier 58 produces a substantially constant voltage at its output (pin 6) which forms terminal $H_1$ which is coupled to the first input $I_1$ of the Hall effect probe 54 of flux sensor 49 of FIG. 8. The non invert operational amplifier input (pin 2) forms field regulator circuit terminal $H_2$ which is coupled to the $I_2$ input of Hall effect probe 54. In this way, a substantially constant current passes into the Hall effect 4 probe at terminal $I_1$ and leaves the probe at terminal $I_2$. A pair of capacitances 67a and 67b each couple a separate one of the output and the invert input of amplifier 58 to circuit ground to filter the current supplied to the Hall effect probe 54 of FIG. 8.

The constant current passing in the Hall effect probe 54 is sensed by an operational amplifier 68 whose invert input (pin 3) is coupled via a resistance 70 to the field regulator circuit 48b output terminal $H_2$ which is connected to terminal $I_2$ of Hall effect probe 54 of flux sensor 49 of FIG. 8. Operational amplifier 68 has its positive and negative power input terminals (pins 11 and 7, respectively) coupled via a separate one of resistances 72a and 72b to the +15 V and −15 V terminals of power supply 48a. A first Zener diode 74a is coupled at its anode to the positive power input (pin 11) of the operational amplifier 68 and at its cathode to circuit ground. A second Zener diode 74b is coupled at its cathode to circuit ground and at its anode to the minus power input (pin 7) of amplifier 68. Together, diodes 74a and 74b lower power dissipation of operational amplifier 68 to improve amplifier stability. The non invert input of operational amplifier 68 (pin 3) is coupled via a resistance 66 to circuit ground. With the amplifier invert input coupled to the Hall effect probe 54 first input terminal $I_2$ and the amplifier non invert input coupled to circuit ground, the amplifier produces a voltage at its output (pin 6) which varies in accordance with the current passing in the Hall effect probe 54. The voltage gain of operational amplifier 68 is established by ratio to the feedback impedance with comprises a pair of capacitance 76a and 76b which are each coupled in parallel with the serial combination of resistances 78a, 78b and 78c across the invert input (pin 2) and output (pin 6) of operational amplifier 68 to the amplifier input impedance (Resistance 70). Resistance 78a is typically made adjustable so as to allow the gain of the operational amplifier to be varied.

The output of operational amplifier 68 is coupled via the parallel combination of resistances 80a and 80b to the invert input (pin 2) of an operational amplifier 82 which is coupled at its positive and negative power inputs (pins 7 and 4) to the +15 V and −15 V terminals of power supply 48a of FIG. 6. The invert input of operational amplifier 82 is also coupled via a resistance 84 to the output of an operational amplifier 86 whose positive and negative power input (pins 7 and 4) is coupled to the +15 V and −15 V terminals of the power supply. Operational amplifier 86 has its invert and non invert inputs (pins 2 and 3, respectively) coupled via resistances 88a and 88b to field regulator circuit terminals $V_1$ and $V_2$ which are connected to the outputs $O_1$ and $O_2$ of Hall effect probe 54 of flux sensor 49 of FIG. 8. Resistances 88a and 88b are mounted to heat sink 66 so that resistances 88a and 88b are held to approximately the same temperature. A pair of capacitances 89a and 89b each couple a separate one of terminals $V_1$ and $V_2$ to circuit ground to filter any extraneous noise. Operational amplifier 86, when supplied at its invert and non invert input with the output voltage of the Hall effect probe 54 produces a signal at its output (pin 6) which is proportional to the Hall effect probe output voltage differential by virtue of the feedback resistance 90a of opertional amplifier 86 which is coupled in parallel between the invert operational amplifier input (pin 2) and the operational amplifier output (pin 6). Capacitances 90b and 90c are coupled in parallel with resistance 90a and reduce the high-frequency gain of operational amplifier 86.

Operational amplifier 82, which has its non invert input (pin 2) supplied with the algebraic sum of the output voltages of operational amplifiers 68 and 86, has its non invert input (pin 3) coupled via a resistance 94 to the center pin of a BNC connector 95 whose sleeve is coupled to circuit ground. In practice, the BNC connector 95 is supplied with the output signal of a ramp generator (not shown) thereby causing the output signal of the amplifier 82 which appears at pin 6 to be ramped accordingly. The output signal of amplifier 82 is supplied to each of coils 20 of FIG. 1a through an amplifier described later. When the output signal of amplifier 82 is ramped by virtue of the ramp signal at the amplifier invert input, the fields produced by each of coils 20 are correspondingly ramped. A capacitance 95a shunts the center pin and sleeve of BNC connector 95 to filter any extraneous noise.

In addition to being supplied with the ramp generator output signal, operational amplifier 82 has its invert input coupled via a resistance 96 to the wiper arm of a potentiometer 97 whose fixed resistance portion is coupled between the positive power input (pin 7) of the operational amplifier (which pin is coupled to +15 V terminal of the power supply 48a) and circuit ground. The negative power input (pin 4) of the operational amplifier is coupled to the −15 V terminal of the power supply 48a. In the absense of any ramp generator signal being coupled via the BNC connector 95 to the operational amplifier invert input, the input signal to the invert input of the operational amplifier is a substantially constant voltage which may be varied by adjusting the variable resistance 97 so that the output signal of the operational amplifier varies directly with the sum of the output voltage of the Hall effect probe 54 and the input current to the Hall effect probe 54. A capacitance 98 shunts the fixed resistance portion of potentiometer 97.

The gain of operational amplifier 82 is determined in part by a feedback impedance 99 includes a resistance 100 and a capacitance 102 serially coupled between the non invert amplifier input (pin 2) and the amplifier output (pin 6). A capacitance 104 has one terminal thereof coupled to the output (pin 6) of the operational amplifier and has its other terminal coupled by a switch 106 to either the input (pin 2) of the operational amplifier or to one terminal of a resistance 108 whose other terminal is coupled to the operational amplifier output. When switch 106 is at the "run" position so that capacitance 104 is coupled in parallel with the series combination of resistance 100 and capacitance 102, then, the feedback impedance 99 exhibits a significant reactance to cause the operational amplifier to operate as an integrater. However, when switch 106 is in the "tune" position, so that capacitance 104 is shunted across resistance 24, then feedback impedance 99 now consists of only resistance 100 in series with capacitance 102 and is thus much less reactive. During start up and adjustment of field controller circuit 48b, it is desirable that the reactance of the feedback impedance be made less reactive as is accomplished when switch 106 is in the "tune" position.

The output signal of operational amplifier 82, is attenuated by a resistance 110 before being supplied to the non-invert input (pin 3) of an operational amplifier 112. The operational amplifier 112 has its invert input (pin 2) coupled to circuit ground via a resistance 114. Each of the positive and negative power input terminals (pins 7 and 4, respectively) of the operational amplifier is coupled via separate resistances 116 and 118, respectively, to the +15 and −15 volt terminals of the power supply. In response to the input signal supplied from operational amplifier 82, operational amplifier 112 supplies an output signal at its output (pin 6) which forms terminal $C_1$ which is connected to each of the electromagnetic coils 20. A capacitance 119 couples the output of amplifier 112 to circuit ground to filter noise. The gain of the amplifier 112 is established by the ratio of the sum of unity plus the feedback resistance 120, coupled between the second input (pin 2) and the output of the operational amplifier, plus one to amplifier input impedance (resistance 114).

In addition to being supplied with the output signal of operational amplifier 112, each of the coils 20 is also supplied with the output signal of a push-pull voltage amplifier comprised of a pair of transistors 122a and 122b. Each of transistors 122a and 122b has its collector-to-emitter portion coupled between a separate one of the +15 V and −15 V terminals, respectively, of the power supply 48a and the output (pin 6) of operational amplifier 112. The collector-to-emitter portion of each transistor is shunted by a separate one of oppositely-poled diodes 124a and 124b so as to be protected from excessive voltage. The transistors 122a and 122b are each coupled at their respective bases via a separate one of resistances 126a and 126b to the power input terminals (pins 4 and the Tab, respectively), of operational amplifier 112 so that each of transistors 122a and 122b is supplied a constant negative current and positive current at its respective base.

When transistors 122a and 122b supplied at their respective bases with a negative and positive current, transistors 122a and 122b supply a constant d.c. voltage at terminal $C_1$ which is coupled to the coils 20 surrounding the pole surface of each magnet 16a and 16b of FIG. 1. The output signal of amplifier 112 which is superimposed on the d.c. voltage produced by the push-pull amplifier and supplied to coils 20, causes the flux produced by coils 20 to vary in accordance with the Hall effect probe 54 output voltage and hence, the flux of magnets 16a and 16b.

What has been described thus far is the portion of the field regulator circuit 48b which regulates the excitation of the electromagnetic coils 20 of FIG. 1A in accordance with the polarizing magnet flux as sensed by the Hall effect probe 54 of flux sensor 49. In addition to the circuitry described thus far, field regulator circuit 48b also includes a circuit, comprised of generally of an operational amplifier 130, for regulating the conduction of power transistor 55 of the flux sensor 49 of FIG. 8 to control the ambient temperature of the Hall effect probe 54 so that the output voltage produced thereby, which represents the polarizing magnet flux, is thermally stabilized. Operational amplifier 130 is coupled at its positive and negative power input terminals (pins 7 and 4) to the +15 V and −15 V terminals of the power supply 44b. The non invert input (pin 3) of amplifier 130 forms the terminal TH of the field controller circuit which is coupled to thermistor 57 of the flux sensor circuit 49 of FIG. 8 A capacitance 131 couples the terminal TH of circuit ground to filter extraneous noise.

The non invert input of operational amplifier 130 is also coupled to the wiper arm and one terminal of the fixed resistance portion of a potentiometer 132. The other terminal of the fixed resistance portion of potentiometer 132 is coupled via a resistance 134 to the +15 V terminal of the power supply. With the non invert input of operational amplifier 130 coupled both to thermistor 57 and to the +15 V terminal of power supply 44a, the voltage at the non invert input of operational amplifier 130 varies in accordance with the impedance of thermistor 57 of flux sensor circuit 49 of FIG. 8 so that the voltage of the invert input of the operational amplifier varies in accordance with the ambient Hall effect probe 54 temperature. The invert input (pin 2) of the operational amplifier is coupled to the junction of resistances 136 and 138 which are coupled in series between the +15 V terminal of the power supply and circuit ground.

The output of the operational amplifier 130 (pin 6) is coupled via a resistance 140 to terminal B of the field regulator circuit which is coupled to circuit ground via a resistance 142 and a capacitance 141 and is also coupled to terminal B of the field regulator circuit which is connected to the base of transistor 55 of flux sensor 49 of FIG. 8. Resistances 140 and 142 thus serve a voltage divider so that only a portion of the output signal of amplifier 130 is supplied to the base of transistor 55. A feedback impedance 144, comprised of capacitor 146 shunted by the series combination of capacitor 148 and a resistance 150, is coupled between the amplifier output (pin 6) and the invert amplifier input (pin 2) and serves to establish the amplifier gain in combination with amplifier input impedance. With amplifier 130 connected in the manner described so that the invert input is supplied with a substantially constant voltage and the non invert input is supplied with a voltage varying in accordance with the thermistor impedance, the amplifier output signal will thus vary in accordance with the flux sensor 54 temperature, to energize transistor 55 accordingly.

TRANSMITTER 21

Figure 9:
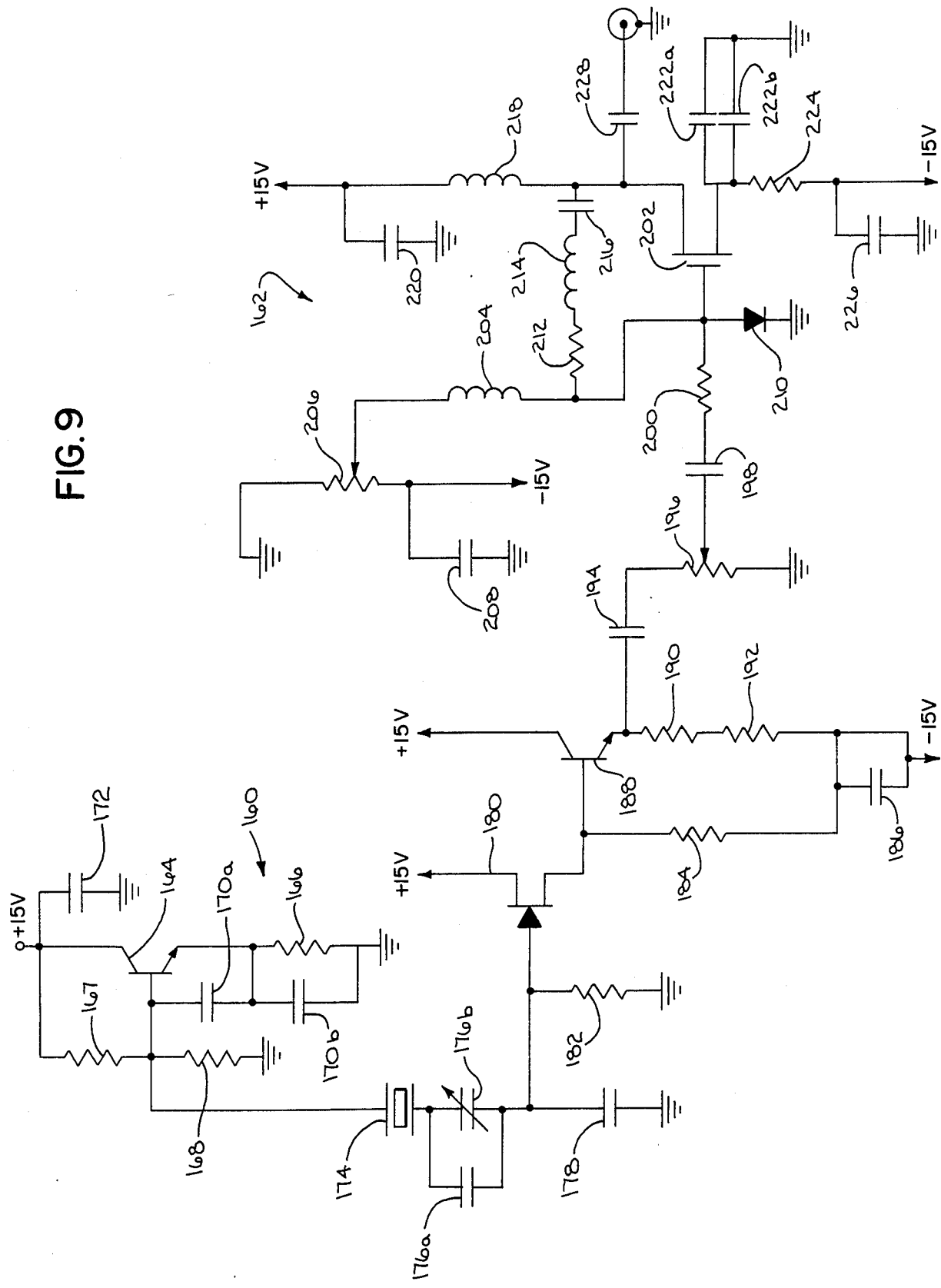
FIG. 9 is a block schematic diagram of the transmitter of the nuclear magnetic resonance blood flowmeter of FIG. 5.

Returning now to FIG. 5, the transmitter 26 which energizes transmitter coil 28 to induce a nuclear magnetic resonance response is comprised of an oscillator 160 and a power amplifier 162. The schematic details of the oscillator 160 and the transmitter 162 are illustrated in FIG. 9. Referring to that figure, the oscillator 160 comprises a transistor 164 whose collector-to-emitter portion is coupled in series with a resistance 166 between the +15 V terminal of a 15 volt power supply (not shown) configured similar to power supply 48a and circuit ground. The transistor 164 has its base coupled via a resistance 167 to the +15 V power supply terminal so that the transistor will be biased from the power supply. A resistance 168, coupled in parallel with a pair of capacitances 170a and 170b, couples the base of transistor 164 to circuit ground to make the transistor self-oscillate. The junction between capacitances 170a and 170b is connected to the junction between resistance 166 and transistor 164. Shunting the series combination of the collector-to-emitter portion of transistor 164 and resistance 166 is a capacitance 172 which filters any noise from the power supply.

The transistor oscillation frequency is stabilized to approximately 3.192 MHz by a quartz crystal 174 coupled between the base of the transistor and the one terminal of a pair of parallel coupled capacitances 176a and 176b. The other terminal of capacitances 176a and 176b is coupled to circuit ground via a capacitance 178. In practice, capacitance 176a is chosen as a variable capacitance so as to allow the oscillator frequency to be set at or about 3.192 MHz.

The power amplifier 162 of transmitter 21 includes a driver section comprised of a field effect transistor 180 whose gate is coupled to the junction between capacitance 178 and capacitances 176a and 176b so as to be supplied with the oscillator output signal. A resistance 182 couples the gate of the field-effect transistor 180 to circuit ground to provide a bias voltage to the transistor. The drain-to-source portion of the field effect transistor 180 is coupled in series with a resistance 184 and a capacitance 186 between the +15 V and -15 V terminals of the power supply.

Field effect transistor 180 has its source terminal coupled to the base of a conventional bi-polar transistor 188 whose collector-to-emitter portion is coupled in series with resistances 190 and 192 between the +15 V and -15 V terminals of power supply. With transistor 188 coupled at its base to the source terminal of field effect transistor 180, the signal at the source of transistor 188 which is proportional to the oscillator output signal, is further amplified by transistor 188, and serves as a buffer between the oscillator 160 and the power amplifier 162.

The output signal of the power amplifier driver section which appears at the emitter of transistor 188 is supplied to a divider network comprised of a capacitance 194 coupled in series of the fixed resistance portion of a potentiometer 196 between the transistor emitter and circuit ground. Potentiometer 196 has its wiper arm coupled by a capacitance 198 in series with a resistance 200 to the gate of a power field effect transistor 202 which generates the radio frequency output signal to drive transmitter coil 28 in accordance with the output signal of oscillator 160. The gate of field effect transistor 202 is supplied with a bias voltage via an inductance 204 which is coupled between the field effect transistor gate and the wiper arm of a potentiometer 206 whose fixed resistance portion is coupled in parallel with a capacitance 208 between the -15 V terminal of the power supply and circuit ground. A diode 210 is coupled between the gate of field effect transistor 202 and circuit ground so as to protect the gate of transistor 202 from the possibility of excessive bias voltage.

Field effect transistor 202 is also supplied with negative feedback at its gate terminal via a resistance 212, an inductance 214 and a capacitance 216 serially coupled between the field effect transistor gate and the field effect transistor drain which is coupled via an inductance 218 to the +15 V power supply terminal. A capacitance 220 couples the junction of inductance 218 and the +15 V terminal of the power supplied to circuit ground so as to filter any noise. The field effect transistor 202 has its source terminal coupled to circuit ground via a pair of parallel coupled capacitances 222a and 222b. A resistance 224 couples the junction of capacitances 222a and 222b and the field effect transistor source to -15 V power supply terminal which is shunted to ground via capacitance 226.

The connection of field effect transistor 202 to the driver circuit in the manner described above causes the field effect transistor 202 to produce a radio frequency signal at approximately 3.192 MHz at its drain terminal. This radio frequency signal is coupled via a capacitance 228 to one terminal of the transmitter coil, the second terminal of the transmitter coil being coupled to circuit ground.

RECEIVER 30

Returning now to FIG. 5, the radio frequency signal produced by the combination of transmitter 26 and radiated by transmitter coil 28 and by modulator 37 and radiated by modulator coil 36 causes the water molecules in the blood to precess and to induce an NMR signal in the flowing blood received in the receiver coil 30 connected to receiver 32. As will become better understood by a further description of the NMR blood flowmeter of the present invention, the deviation in the receiver output signal can be utilized to effectively measure blood flow. In order to reduce any remnant leakage of the transmitter's signal, the receiver 32 of the present invention is a single side band receiver which is tuned to a side band the transmitter signal radiated by transmitter coil 28. To enable reception by the receiver of a side band signal, the $B_o$ field of the polarizing magnets is modulated by way of a modulator 37 which typically takes the form of an 8 KHz audio-oscillator which drives modulator coil 36. The sum or difference of the transmitter frequency, typically 2,565 kHz, and the modulator frequency, typically 8 kHz, is the side band frequency.

The details of the receiver 32 are illustrated in block form in FIG. 10. Referring to that figure, the receiver includes a first crystal band pass filter 250 coupled between the receiver coil 30 and the input of a radio frequency amplifier 252 for passing to the radio frequency amplifier only one side band (2.573 MHz) of the combined transmitter signal and modulator signal received in coil 30 (which is at a frequency equal to the sum or difference of the transmitter frequency $f_o$ which as indicated is 2.565 MHz plus the modulator frequency $f_{mod}$ which is 8.0 KHz) while rejecting the transmitter frequency $f_o$. Typically, the upper sideband (2.573 MHz) is used. The output of the RF amplifier 252 is coupled to a second band pass filter 254 which further filters the radio frequency amplifier output signal before it is supplied to the first input of a mixer 256. The second input of mixer 256 is supplied with the output signal of a local oscillator 258. The frequency of the local oscillator is typically 3.028 MHz so that the frequency of the mixer output signal, which equals the difference between the received signal of 2.565 MHz and the local oscillator signal of 3.028 MHz is approximately 455 kHz. An intermediate frequency (IF) filter and an amplifier 260 amplify the output signal of the mixer 256 to yield the 455 kHz intermediate frequency output signal of the receiver which is supplied to a synchronized phase detector 33 (FIG. 5) which detects the induced nuclear magnetic resonance response, in accordance with deviations in the receiver output signal.

SYNCHRONIZED DETECTOR 33

The details of synchronized detector 33 are illustrated in block form in FIG. 11. Referring to that figure, the synchronized phase detector 33 includes a phase lock filter 264 which is supplied at its input with a reference intermediate frequency signal derived by a triple mixer 266 from a combination of the transmitter signal, the local oscillator signal of the receiver and the modulator signal. In practice, the triple mixer 266 comprises a first mixer 268 which combines the transmitter signal of approximately 2.565 MHz with the local oscillator signal of the receiver which is approximately 3.028 MHz to yield a signal varying in accordance with the difference in frequency therebetween. The output signal of mixer 268, typically about 463 KHz, is combined at a second mixer 270 with the modulator signal which is approximately 8.0 KHz to yield a reference intermediate frequency signal of approximately 455 KHz.

The 455 KHz output signal of triple mixer 266 is supplied to the input of the phase lock filter 264 of detector circuit 33 which locks the phase of the reference intermediate frequency signal. The output signal of phase lock filter 264 is supplied to a variable phase shifter 272. Variable phase shifter 272 allows the phase of the reference intermeidate frequency signal produced by phase lock filter 264 to be varied between zero and 180 degrees so as to allow the detected quadrature phase or in phase nuclear magnetic resonance response to be maximized while the other is minimized. The output of variable phase shifter 272 is coupled to the first input of a first switching detector 274a whose second input is coupled to receiver 32 of FIG. 10 so as to receive the receiver intermediate frequency output signal. Switching detector 274a detects the in-phase nuclear magnetic resonance response in accordance with the interaction between the receiver intermediate frequency output signal and the reference intermediate frequency signal produced by phase shift 272. The output signal of switching detector 274a is filtered by a low pass filter 276a before being supplied to filter and amplifier 278 of FIG. 5.

A second switching detector 274b for detecting the quadrature phase has its first input coupled in parallel with the first input of switching detector 274a so as to receive the intermediate frequency output signal of receiver 32 of FIG. 10. The second input of switching detector 274b is coupled via a 90 degree phase shifter 280 to the output of the variable phase shifter 272 so that the intermediate frequency reference signal received by switching detector 274b is phase shifted 90 degrees from the reference intermediate frequency signal supplied to switching detector 274a. A low pass filter 276b filters the output signal of switching detector 274b before it is supplied to the filter and amplifier 278.

Both of switching detectors 274a and 274b have a disable input D. When supplied with a logic high level voltage at its disable input, each of the switching detectors becomes disabled. Normally, both of switching detectors 274c and 274b are enabled by a low logic level voltage to enable the synchronized detector to detect the induced NMR response. However, it is desirable during intervals when the tag coil 38 is energized from tag circuit 39 to disable each of the switching detectors so that the receiver does not detect a false NMR response. This is accomplished by applying a high logic level voltage at the disable input D of each detector.

Returning now to FIG. 5, the output signal of filter and amplifier 278, which varies in accordance with either the in phase or quadrature phase induced nuclear magnetic resonance response depending on how variable phase shifter 272 is adjusted, is supplied to a data averaging computer 284 which typically takes the form of a model 7100 data retrieval computer as manufactured by Chicago Nuclear Corporation, Des Plaines, Ill. Data averaging computer 284 operates to receive the output signal of amplifier and filter 278 and to convert the analog information into digital information which is stored in the computer memory. This is repeated N times, with the analog information added to computer memory. The digital information stored in the computer memory is then retrieved and, by repeatedly addressing the computer memory locations where the digital information is stored, the noise is reduced by a factor of N (square root of the number of averages). The retrieved digital information is then displayed on the computer analog display which takes the form of a cathode ray tube. Although other means, such as a oscillograph or oscilloscope could be supplied with output signal of amplifier 278 and thus display the induced nuclear magnetic resonance response, it is desirable to use an averaging computer such as computer 284 to relieve any noise present at the output of amplifier 278.

The nuclear magnetic resonance blood flowmeter described thus far can be employed to advantageously measure pulsatile arterial blood flow. As the water molecules of the blood flowing in the limbs supported by lumen 22 of FIG. 1 pass through the magnetic field of polarizing magnets 16a and 16b, the polarizing magnets polarize the hydrogen atoms of the blood water molecules so that slightly more are aligned parallel to the field than are aligned anti-parallel to the field. As the blood moves past the transmitter coil 28, some of the hydrogen atoms of the blood water molecules aligned with the magnetic polarizing field absorb energy radiated by the transmitter coil 28 so as to flip and become aligned anti-parallel to the polarizing field thus tending to equalize the parallel and anti-parallel populations. When enough of the hydrogen atoms flip to become aligned anti-parallel to the polarizing field so as to equalize the populations, the net nuclear magnetization becomes zero, and the hydrogen atoms are said to become saturated. Normally, saturation would occur very rapidly in the absence of the modulation field. However, the presence of the modulation field causes the saturation rate to be reduced because saturation occurs during only a brief portion of the modulation cycle.

Because arterial blood flow tends to be pulsatile, high blood flow occurs only during intervals of systolic flo intervals with low blood flow occurring during diastolic flow intervals. During diastolic blood flow intervals, the saturated hydrogen atoms of the blood water molecules in the region of the receiver coil 30 yield a low NMR response so that the deviation in the receiver 32 output signal will be less in magnitude than during intervals of systolic blood flow when magnetized nuclei pass into the region of the receiver region from upstream. Thus the variation in the output signal amplified of amplifier and filter 278 is related directly to the pulsatile component of blood flow. By adjusting the DC offset of each of filters 276a and 276b of 278 as illustrated in FIG. 11, the nuclear magnetic resonance response of the tissue surrounding the vessel through which the blood is flowing can be subtracted from the amplifier output signal to yield an accurate representation of arterial blood flow.

Venous blood flow is not pulsatile in contrast to arterial blood flow so that the "self-tag" method for measuring blood flow described above is not suitable to measure venous blood flow, without a method of separating the steady flow response from the steady tissue response. Such a method is described later when two dimensional scanning is discussed. To measure venous blood flow, a bolus of venous blood is "tagged" or demagnetized upstream of the receiver coil so that the tag bolus can be later detected at the receiver coil. To this end, the tag coil 38 is carried by lumen 22 upstream (distally on the human limb) of the transmitter and receiver coils is energized with a radio frequency signal at or near the Larmor frequency by tag circuit 39 so as to demagnetize the bolus of blood. Returning to FIG. 5, tag circuit 39 is comprised of a radio frequency signal generator 288, typically a Boonton model 102 radio frequency signal generator, whose output is coupled to the input of power amplifier 289. The power amplifier 289 which typically comprises an Electronic Navigation Industries model 310L power amplifier excites tag coil 38 in accordance with the radio frequency signal generator output signal.

TAG SELECT CIRCUIT 290

The tag circuit 39 also includes a tag select circuit 290 which is coupled to the disable input D of both of the switching detectors 274a and 274b of phase detector 33 and to radio frequency signal generator 288 and advantageously disables the phase detectors just before, during and immediately after generation of a tag signal so that the tag signal will not cause interference with the detected receiver signal. The details of the tag circuit are illustrated in block form in FIG. 12a. Referring to FIG. 12a, tag select circuit 290 includes a pulse generator 292 for generating periodic pulses. The output of pulse generator 292 is coupled to the first input of a two input OR gate 294 whose output is coupled to the disable input D of switching detectors 274a and 274b of FIG. 11. When OR gate 294 is enabled, the presence of a logical high level voltage at the OR gate output results in the each of switching detectors 274a and 274b being disabled for so long as the OR gate remains enabled.

The pulse generator 292 is also coupled at its output to the input of a monostable or one shot multi-vibrator circuit 296. Multi-vibrator circuit 296, when strobed by a pulse generator 292, produces an output signal for a predetermined duration which, as seen hereinafter, is equal to the duration of the tag signal. For this reason multivibrator circuit 296 is referred to as the tag duration multivibrator circuit. The output of monostable circuit 296 is supplied to the input of a second monostable or one shot multi-vibrator circuit 298 as well as being supplied to the first input of a second OR gate 300 whose output is coupled to the second input of OR gate 294. Like monostable or one shot multi-vibrator circuit 296, monostable circuit 298 produces an output pulse for a predetermined duration following the receipt of a signal at its input. As will become clear from a description of the operation of the tag select circuit, monostable circuit 298 renders the detector inoperative for a predetermined time following the tag signal. For this reason, monostable circuit 298 is referred to as the post tag duration monostable circuit.

The output of the tag duration monostable circuit 296 is also coupled to the input of a buffer amplifier 302 whose output is coupled to input of the radio frequency signal generator 288 of FIG. 5. During intervals while the output signal of the tag duration monostable circuit 296 is at a high logic level, then the buffer amplifier 302 outputs a signal of sufficient magnitude to energize the radio frequency signal generator 288 so that the radio frequency signal generator 288 excites the power amplifier 289 which in turn energizes the tag coil 39. The magnitude of the buffer amplifier output signal is controlled by the magnitude of the offset signal supplied to the buffer amplifier 302 from an offset signal generator (not shown).

The operation of tag select circuit 290 may best be understood by reference to FIG. 12b which is a timing diagram for the tag circuit 290. Referring to that figure, each time that pulse generator 292 produces a pulse at its output, a logic high level voltage appears at the first input of OR gate 294 causing the OR gate to output a logic high level voltage so that the switching detectors 274a and 274b of phase detector 33 are disabled. Thus, upon the generation of an output pulse by the pulse generated at time $T_o$, phase detector 33 is effectively disabled. Tag duration monostable circuit 296 does not generate an output signal immediately on the generation of an output pulse by the pulse generator, but rather trigger at the falling edge of the pulse. As a result, a brief interval occurs between the time $T_o$ when the pulse generator produces an output pulse and the time $T_1$ when the tag duration monostable circuit supplies a logic high level output signal to buffer amplifier 302. When the buffer amplifier is enabled from the tag duration monostable circuit, the buffer amplifier energizes the radio frequency generator 288 so as to excite the power amplifier 289 which energizes the tag coil 38. Thus, during the preblank interval between $T_o$ and $T_1$, the phase detector 282 is effectively disabled even before a tag signal is generated.

Immediately upon the generation of an output signal by tag duration monostable circuit 296, the output signal of OR gate 300, which had previously been at a logic low level voltage, changes to a logic high level voltage so that a logic high level voltage appears at the second input to OR gate 294 to cause the output signal of OR gate 294 to remain at a logic high level even after the output pulse produced by pulse generator 292 has decayed to a zero amplitude. During the interval between time $T_1$ and a later time $T_2$ while the output signal of tag duration monostable circuit 296 remains at a logic high level voltage, OR gate 300 remains enabled and thereby produces a logic high level voltage at its output. With the output voltage at OR gate 300 at a logic high level during this interval of the duration of monostable circuit 296 output pulse, the output voltage of OR gate 294 also remains at a logic high level to effectively disable phase detector 33. Thus, during the "tag-on" interval between $T_1$ and $T_2$, the phase detector remains effectively disabled.

The post-tag duration monostable circuit 298 also becomes enabled but only after tag duration monostable 296 returns to zero. As a result of the post tag duration monostable circuit 298 being enabled at the end time, $T_2$, of tag duration monostable circuit 296, the output signal of tag duration monostable circuit 298 remains at a logic high level voltage until time $T_3$. Thus, the second input to OR gate 300 also remains at a logic high level voltage for the interval between $T_2$ and $T_3$, notwithstanding the change in the voltage level at the first input to OR gate 300 to logic low level voltage so that a high logic level voltage remaining at the OR gate output. A logic high level voltage at the output of OR gate 300 causes the output voltage of OR gate 294 to remain at a high logic level so that the phase detector 282 effectively remains disabled until time $T_3$ when the output voltage of post tag duration monostable circuit 298 changes to a logic low level voltage. In this way, the phase detector 33 is effectively disabled by tag select circuit 290 just before, during and just after the generation of a tag signal to reduce interference between the tag signal and the transmitter signal.

SCANNER CIRCUIT 47

As alluded to previously, the coils 44a and 44b of each of scanning coil sets 42a and 42b, the coils of scanning coil pair 46a and 46b are each coupled to a scanner circuit 45 which controls the current in each of the coils. The scanner circuit 45, described in greater detail below with respect to FIG. 14, controls the current in each of the scanning coil sets 42a and 42b and the current each of the coils 46a and 46b to effectively range or focus the nuclear magnetic resonance response in two dimensions to enable blood flow measurement within a single artery or vein along a particular base line. To better understand how scanner circuit 45 accomplishes two-dimensional scanning or ranging of the limb, reference should be had to the paper "Ranging for Individual Artery Flow in the Nuclear Magnetic Resonance Flow Meter" by Richard E. Halbach, et al. published in the conference record of the IEEE, 1980 Frontiers of Engineering and Health Care Conference held at Washington, D.C., Sept. 29, 1980 at pages 356-359 which describes a nuclear magnetic resonance blood flowmeter which accomplishes one dimensional scanning or ranging of the limb. As described in that paper, the induced nuclear magnetic resonance response of a nuclear magnetic resonance blood flowmeter can be cancelled everywhere except along a null plane by energizing each of a pair of scanning coils disposed on opposite sides of the flow lumen with opposite polarity currents. By varying the ratio of current in each of the scanning coils, the null plane where the opposing magnetic fields from the scanner coils tend to cancel each other, can be effectively shifted through the lumen. In the presently preferred embodiment, the general principles set forth in the Halbach et, al. paper have been utilized to accomplish two dimensional scanning of the limb.

The details of scanning circuit 45 are illustrated in block form in FIG. 13. Turning now to FIG. 13, scanner circuit 45 comprises a pair of saw tooth generators 312a and 312b, one saw tooth generator generating a saw tooth output signal whose frequency is much greater than the other. The amount of offset or DC in the saw tooth generator output signal is controlled by the magnitude of the bias voltage supplied to each saw tooth generator. The output signal of generator 312a supplied to the first input $I_1$ of a multiplier 314a which modulates the signal at its first input $I_1$ in accordance with the sinusoidal signal supplied to the second input $I_2$ of the multiplier. The output signal of multiplier 314a is amplified by amplifier 318a before being supplied to scanning coils 44a and 44b of scanning coil set 42a. An inverter 319a couples the output of saw tooth generator 312a to first input $I_1$ of a multiplier 314b which modulates the signal at its first input $I_1$ in accordance with the sinusoidal signal at the second multiplier input $I_2$. The output of multiplier 314b is coupled to a power amplifier 318b which energizes scanning coils 44a and 44b of scanning coil set 42b in accordance with the output signal of multiplier 314b.

Saw tooth generator 312b has its output coupled to the first input $I_1$ of a multiplier 314c which modulates the signal at its input $I_1$ in accordance with the sinusoidal signal at its $I_2$ input. The output of multiplier 314c is coupled to the input of a power amplifier 318c which energizes scanning coil 46a in accordance with the multiplier output signal. An inverter 319b couples the output of saw tooth generator 312b to the first input $I_1$ of a multiplier 314d which modulates the signal at its $I_1$ input in accordance with the sinusoidal signal at its second input $I_2$. Both of the multipliers 314c and 314d are supplied with sinusoidal signals at their respective $I_2$ inputs which are at the same frequency, but phase-shifted 90° from the sinusoidal signals at each of the $I_2$ inputs of multipliers 314a and 314b. The output of multiplier 314d is coupled to the input of a power amplifier 318d which energizes the scanning coil 46b with a current to produce a magnetic field opposite in polarity to the magnetic field produced by the current supplied by a power amplifier 318c to scanning coil 46a.

Similarly, coil sets 42a and 42b are energized with currents to produce fields in the region of detection of polarity opposite to each other.

Figure 14A:
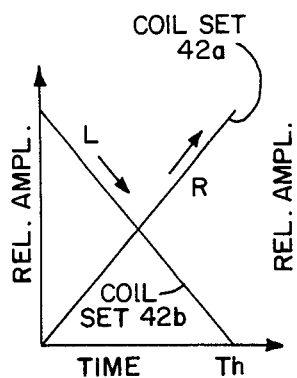
FIGS. 14a–14d graphically illustrate the relationship of the current amplitude in the scanning coils of the blood flowmeter of FIG. 1 as a function of time.
Figure 14B:
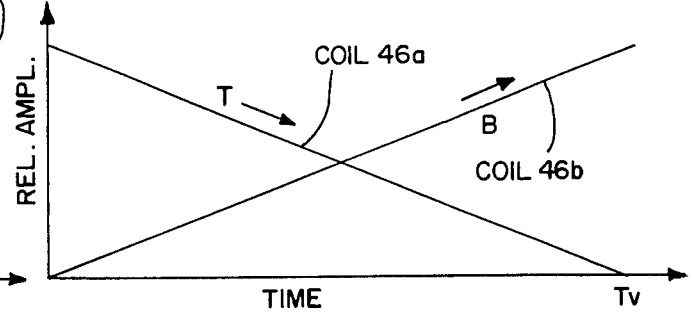

The relationship between the relative current amplitude in each of the scanning coil sets 42a and 42b is illustrated graphically in FIG. 14a for the condition of a zero amplitude bias voltage at saw tooth generator 312a. As illustrated in that figure, as the amplitude of the sawtooth output signal of sawtooth generator 312a increases, the relative sinusoidal current magnitude in the coils of scanning coil set 42a increases in amplitude while the relative sinusoidal current amplitude in the scanning coils of scanning coil set 42b decreases in amplitude. Referring now to FIG. 14b, as the amplitude of the sawtooth output signal of sawtooth generator 312b increases in amplitude, the relative amplitude of current in scanning coil 46a decreases while the relative amplitude of current in scanning coil 46b increases. The sinusoidal input to multiplier 314a, 314b, 314c and 314d is typically the same frequency (approximately 125 Hz) but with a 90° phase shift between that input driving 314a and 314b and that input driving 314c and 314d. Alternatively, instead of using the same frequency for coil sets 42 and 46 with a 90° phase shift in currents between them, two separate frequencies may be used.

Figure 14C:
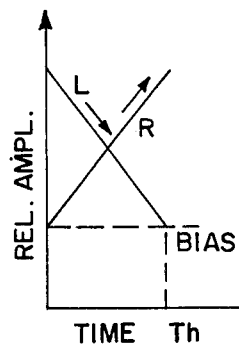
Figure 14D:
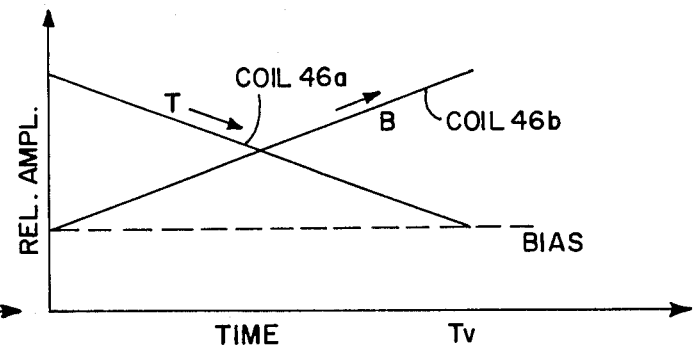

Referring now to FIG. 14c, when a d.c. bias voltage is supplied to sawtooth generator 312a, the current in the coils of scanning coil set 42a increases linearly above a fixed current amplitude, which is proportional to the bias voltage as the amplitude of the sawtooth output signal of sawtooth generator 312a increases in contrast to the condition of a zero bias voltage illustrated in FIG. 14a where the scanning coil relative current amplitude increases from a zero value as the amplitude of the sawtooth output signal increases. With a net d.c. bias voltage applied to the sawtooth generator, the relative current amplitude in scanning coil set 42b will decrease to a value proportional to the bias voltage, rather than a zero value as illustrated in 14b when the amplitude of the sawtooth output signal of sawtooth generator 312a has increased to its maximum amplitude. Referring now to FIG. 14d, the application of a bias voltage to sawtooth generator 312b causes the current in scanning coil 46b to increase linearly above a current amplitude proportional to the bias voltage as the saw tooth generator output signal amplitude increases rather than to increase from a zero current amplitude in response to an increase in the amplitude of the sawtooth output signal of the saw tooth generator. Conversely, as saw tooth generator output signal amplitude rises in time, the current in scanning coil 46a decreases linearly to a value proportional to the d.c. bias voltage rather decreasing to zero as would be the case without such bias voltage.

Linearly varying each of the opposing currents in scanning coil sets 42a and 42b and scanning coils 46a and 46b in accordance with a saw tooth wave form modulating a sinusoidal signal causes the line of intersection of each of the respective null planes, where the fields of scanning coil sets 42a and 42b and scanning coils 46a and 46b tend to cancel each other, to effectively scan the lumen from left to right simultaneously while scanning the lumen top to bottom in much the same way as a television screen is scanned with a raster scan signal. The two dimensional scanning of its lumen in this manner advantageously enables the NMR response to be focused through a single artery or vein to the exclusion of all others to enable blood flow measurement within the artery or vein along a particular base line.

Figure 15:
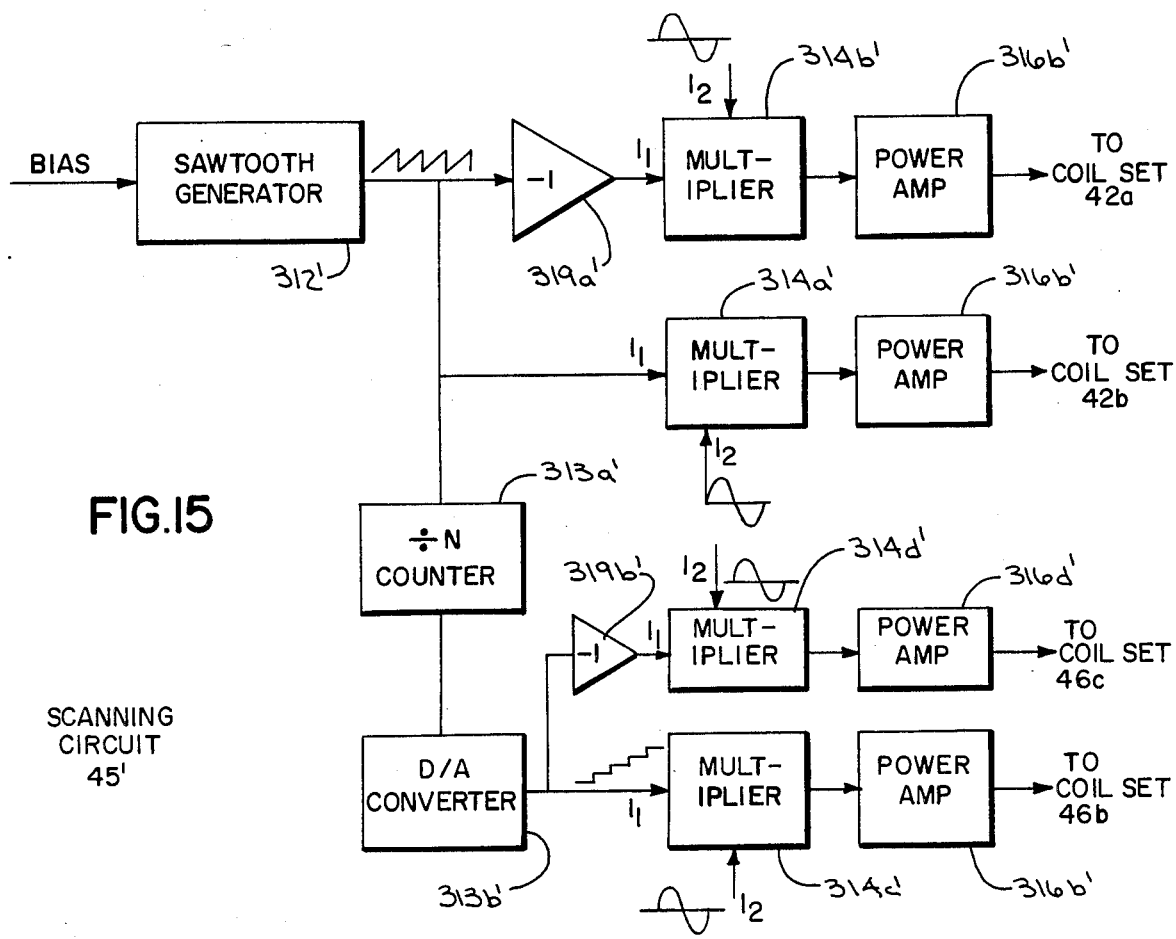
FIG. 15 is an alternate preferred embodiment of a scanner control circuit for the NMR blood flowmeter of FIG. 1.

An alternate embodiment 45' of a scanning circuit for controlling the current in each of the coils of scanning coil sets 42a and 42b and for controlling the current in coils 46a and 46b is illustrated in FIG. 15. Referring to that figure, scanning circuit 45' comprises a saw tooth generator 312' which produces a saw tooth output signal. The saw tooth generator output signal is supplied directly to the $I_1$ input of a first multiplier 314a which modulates the input at its $I_1$ input in accordance with the sinusoidal signal at its $I_2$ input. The output signal of the sawtooth generator 312' is also supplied through an inverter 319' to the $I_1$ input of a second multiplier 314b' which modulates its input signal in accordance with the sinusoidal signal at its $I_2$ input. Each of a pair of power amplifiers 316a' and 316b' is coupled to a separate one of the coils 44a and 44b of scanning coil sets 42a and 42b and supplies the scanning coil set with current in accordance with the output signal of a separate one of multipliers 314a' and 314b'.

In comparison with scanning circuit 45 of FIG. 13, identical components are employed in scanning coil circuit 45' to excite each of coils 44a and 44b of scanning coil sets 42a and 42b so that the sinusoidal current in scanning coil set 42a increases linearly as the saw tooth generator output signal rises in amplitude while the sinusoidal current in scanning coil set 42b decreases linearly in amplitude during intervals while the saw tooth generator output signal rises in amplitude.

Scanning circuit 45' differs from scanning circuit 45 of FIG. 13 in that scanning circuit 45' energizes each of coils 46a and 46b with a staircase modulated sinusoidal signal rather than a sawtooth modulated sinusoidal signal. In place of the saw tooth generator 312b of FIG. 13, scanning circuit 45' of FIG. 15 has a divide by N counter 313a' whose input is coupled to the output of saw tooth generator 312'. The digital output count of divide by N counter 313a', which is equal to 1/N of the frequency of saw tooth generator 312', is supplied to the input of a digital to analog convertor 313b'. The digital to analog convertor output signal, which appears as a staircase signal, is supplied to the $I_1$ input of a multiplier 314c' which modulates its input signal in accordance with a sinusoidal signal at the multiplier $I_2$ input, which is phase-shifted 90° from the sinusoidal signal at the $I_2$ input of multiplier 314a' and 314b'. The staircase output signal of digital to analog converter is also supplied to the input of an inverter 319b' whose output is coupled to the $I_1$ input of a second multiplier 314d' which modulates its output signal in accordance with a sinusoidal signal at its $I_2$ input which is phase-shifted 90° from the sinusoidal signal at the $I_2$ input of multiplier 314a and 314b. The output of each of multipliers 314c' and 314d' is coupled to input of a respective one of power amplifiers 316c' and 316d', respectively. Each of power amplifiers 316c' and 316d' is coupled at its output to a separate one of scanning coils 46b and 46a, respectively, to energize the scanning coil with a signal in accordance with the input signal from a respective one of multipliers 314c' and 314d'. Exciting each of scanning coils 46a and 46b with a sinusoidal signal modulated by a staircase signal as opposed to a saw tooth signal results in the displayed NMR response being of horizontally scanned lines as opposed to a normal raster scan which is achieved by scanning circuit 45 of FIG. 13.

The foregoing describes an improved nuclear magnetic resonant blood flowmeter for non-invasively measuring blood flow. The blood flowmeter of the present invention is capable of two dimensional ranging so at to allow blood flow measurement with a vein or artery along a base line to the exclusion of all other arteries or veins.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

What is claimed is:

1. An improved nuclear magnetic resonance blood flowmeter for non-invasively measuring blood flow in a human limb comprising:
 polarizing magnet means for generating a substantially uniform magnetic field;
 a limb receiving lumen for supporting a human limb within the field generated by said polarizing magnet means so that blood molecules within the limb are magnetically polarized thereby;
 transmitter means located adjacent said lumen for inducing a nuclear magnetic resonance response in the blood molecules of the human limb disposed within said lumen;
 scanning means including:
 first means for generating a first pair of opposing magnetic fields within said lumen for cancelling the nuclear magnetic resonance response induced by said transmitter means everywhere except within a first null plane along which said first opposing magnetic fields cancel each other;

second means for generating a second pair of opposing magnetic fields which are each at a preselected angle to each of the magnetic fields of said first pair of opposing magnetic fields for cancelling the nuclear magnetic resonance response everywhere along a second null plane at which said second pair of opposing magnetic fields cancel each other, said second null plane being at said preselected angle to said first null plane so that a nuclear magnetic resonant response occurs only along a line formed by the intersection of said first and second null planes;

control means coupled to said first and second means for generating said first and second pair of opposing magnetic fields for varying the strength of the opposing magnetic field generated by said first and second means for generating said first and second pair of opposing magnet fields to shift the location of said first and second null planes across said lumen so as to displace said line of intersection of said null planes through the human limb disposed in said lumen;

detector means disposed in part in said lumen for detecting the nuclear magnetic resonance response induced in said lumen and for generating an output signal which varies in accordance with blood flow through said limb;

wherein said polarizing magnet means includes:

first and second oppositely poled magnets, located on opposite sides of said lumen for producing a magnetic field which permeates said lumen; and field stabilizer means carried in part by each of said first and second magnets for stabilizing the field produced thereby so as to maintain a substantially constant field between said first and second magnets, said field stabilizer means having first and second electromagnetic coils each located on the pole face of a separate of said first and second magnets, a temperature-compensated field controller circuit coupled to each of said first and second electromagnetic coils for energizing said first and second electromagnetic coils in accordance with the magnetic field present between said first and second magnets to maintain stability of the magnetic field, and a pair of magnetic shims each circumscribing the pole face of a separate one of said first and second oppositely poled magnets for maintaining coarse homogeneity of the field of each respective magnet;

wherein said temperature-compensated field controller circuit comprises:

a flux sensor disposed within the magnetic field of said first and second magnets for providing an output signal which varies in accordance with the magnetic field of said first and second magnets;

means in thermal contact with said flux sensor for maintaining said flux sensor at a substantially constant temperature; and amplifier means coupled to said flux sensor and to each of said first and second electromagnetic coils for energizing said electromagnetic coils in accordance with the flux sensor output signal.

2. The blood flowmeter according to claim 1 wherein said flux sensor comprises a Hall effect probe.

3. The blood flowmeter according to claim 1 wherein said means in thermal contact with said flux sensor for maintaining said flux sensor at a substantially constant temperature comprises:

a temperature-responsive element in thermal contact with said flux sensor for providing an impedance thereacross whose magnitude changes in response to to temperature changes of said flux sensor;

a heater in thermal contact with said flux sensor for heating said flux sensor; and an amplifier coupled to said temperature-responsive element and said heater for energizing said heater in response to the impedance of said temperature-responsive element so as to maintain the temperature of said flux sensor substantially constant.

4. The blood flowmeter according to claim 3 wherein said heater comprises a power transistor in thermal contact with said flux sensor so that as said transistor is energized, said transistor heats said flux sensor.

5. An improved nuclear magnetic resonance blood flow-meter for non-invasively measuring blood flow in a human limb comprising:

(a) polarizing magnet means for generating a substantially uniform magnetic field;

(b) a limb receiving lumen for supporting a human limb within the field generated by said polarizing magnet means so that blood molecules within the limb are magnetically polarized thereby;

(c) transmitter means located adjacent said lumen for inducing a nuclear magnetic resonance response in the blood molecules of the human limb disposed within said lumen, said transmitter means including i. a transmitter coil disposed about said lumen so that the field produced by said transmitter coil is orthogonal to the field produced by said polarizing magnet, ii. a transmitter including:

an oscillator for producing a radio frequency signal;

a power amplifier coupled to said transmitter coil and to said oscillator for energizing said transmitter coil in accordance with said oscillator output signal;

iii. a modulator coil disposed about said lumen concentric with said transmitter coil but oriented so that the field of said modulator coil is parallel to the field of said polarizing magnet means, and iv. a modulator coupled to said modulation coil for energizing said modulation coil with a periodic frequency substantially below the frequency of said transmitter;

(d) scanning means including:

i. first means for generating a first pair of opposing magnetic fields within said lumen for cancelling the nuclear magnetic resonance response induced by said transmitter means everywhere except within a first null plane along which said first opposing magnetic fields cancel each other, said first means including: a pair of scanning coils each located on opposite sides of said lumen and wherein said second means for generating a second pair of opposing magnetic fields comprises a second pair of scanning coils, each of said scanning coils of said second pair of scanning coils being disposed of opposite sides of said lumen so as to be at a preselected angle with a separate one of the scanning coils of said first pair of scanning coils;

ii. second means for generating a second pair of opposing magnetic fields which are each at a preselected angle to each of the magnetic fields of said first pair of opposing magnetic fields for cancelling the nuclear magnetic resonance response everywhere along a second null plane at which said second pair of opposing magnetic fields cancel each other, said second null plane being at said preselected angle to said first null plane so that a nuclear magnetic resonant response occurs only along a line formed by the intersection of said first and second null planes; and iii. control means coupled to said first and second means for generating said first and second pair of opposing magnetic fields for varying the strength of the opposing magnetic fields generated by said first and second means for generating said first and second pair of opposing magnet fields to shift the location of said first and second null planes across said lumen so as to displace said line of intersection of said null planes through the human limb disposed in said lumen; and (e) detector means disposed in part in said lumen for detecting the nuclear magnetic resonance response induced in said lumen and for generating an output signal which varies in accordance with blood flow through said limb; and wherein said scanning means control circuit comprises:

a saw tooth generator for producing a saw tooth waveform at its output;

first circuit means for modulating the saw tooth generator output signal with a first sinusoidally varying signal and for energizing one of the scanning coils of said first pair of scanning coils in accordance with the sinusoidally modulated saw tooth generator output signal;

a first inverter having its input coupled to the output of said saw tooth generator for producing a signal at the output of the inverter which is phase shifted from the signal at the inverter input;

second circuit means having an input coupled to the output of said inverter for modulating the saw tooth generator output signal with said first sinusoidally varying signal and for energizing the other scanning coil of said first pair of scanning coils in accordance with the sinusoidally modulated saw tooth generator output signal;

a second saw tooth generator for producing a second saw tooth waveform at its output;

a second inverter having its input coupled to the output of said second saw tooth generator for producing a signal at the output of said second inverter which is phase shifted from said second saw tooth generator output signal;

third circuit means for modulating the output signal of said second inverter with a second sinusoidally varying signal phase shifted from said first sinusoidally varying signal and for energizing said one scanning coil of said second pair of scanning coils in accordance with said modulated output signal of said second inverter; and fourth circuit means for modulating the output signal of said second saw tooth generator with said second sinusoidally varying signal and for energizing said other of said scanning coil of said second pair of scanning coils in accordance with the said sinusoidally tooth generator output signal waveform.

6. An improved nuclear magnetic resonance blood flowmeter for non-invasively measuring blood flow in a human limb comprising:

(a) polarizing magnet means for generating a substantially uniform magnetic field;

(b) a limb receiving lumen for supporting a human limb within the field generated by said polarizing magnet means so that blood molecules within the limb are magnetically polarized thereby;

(c) transmitter means located adjacent said lumen for inducing a nuclear magnetic resonance response in the blood molecules of the human limb disposed within said lumen, said transmitter means including i. a transmitter coil disposed about said lumen so that the field produced by said transmitter coil is orthogonal to the field produced by said polarizing magnet, ii. a transmitter including:
an oscillator for producing a radio frequency signal;
a power amplifier coupled to said transmitter coil and to said oscillator for energizing said transmitter coil in accordance with said oscillator output signal;

iii. a modulator coil disposed about said lumen concentric with said transmitter coil but oriented so that the field of said modulator coil is parallel to the field of said polarizing magnet means, and iv. a modulator coupled to said modulation coil for energizing said modulation coil with a periodic frequency substantially below the frequency of said transmitter;

(d) scanning means including:

i. first means for generating a first pair of opposing magnetic fields within said lumen for cancelling the nuclear magnetic resonance response induced by said transmitter means everywhere except within a first null plane along which said first opposing magnetic fields cancel each other, said first means including: a pair of scanning coils each located on opposite sides of said lumen and wherein said second means for generating a second pair of opposing magnetic fields comprises a second pair of scanning coils, each of said scanning coils of said second pair of scanning coils being disposed of opposite sides of said lumen so as to be at a preselected angle with a separate one of the scanning coils of said first pair of scanning coils;

ii. second means for generating a second pair of opposing magnetic fields which are each at a preselected angle to each of the magnetic fields of said first pair of opposing magnetic fields for cancelling the nuclear magnetic resonance response everywhere along a second null plane at which said second pair of opposing magnetic fields cancel each other, said second null plane being at said preselected angle to said first null plane so that a nuclear magnetic resonant response occurs only along a line formed by the intersection of said first and second null planes; and iii. control means coupled to said first and second means for generating said first and second pair of opposing magnetic fields for varying the strength of the opposing magnetic fields generated by said first and second means for generating said first and second pair of opposing magnet fields to shift the location of said first and second null planes across said lumen so as to displace said line of intersection of said null planes through the human limb disposed in said lumen; and (e) detector means disposed in part in said lumen for detecting the nuclear magnetic resonance response induced in said lumen and for generating an output signal which varies in accordance with blood flow through said limb; and wherein said scanning means control circuit comprises:

a saw tooth generator for generating a signal at its output having a saw tooth waveform;

first circuit means for modulating the output signal of said saw tooth generator with a first sinusoidally varying signal and for energizing said scanning coil in accordance with said sinusoidally modulated saw tooth generator output signal;

an inverter having an input coupled to the output of said saw tooth generator for producing a signal at the output of said inverter which is phase shifted from the output signal of said saw tooth generator;

second circuit means for modulating the output signal of said inverter with said first sinusoidally varying signal and for energizing the other of said scanning coils in accordance with said sinusoidally modulated inverter output signal;

a divide by N counter having an input coupled to the output of said saw tooth generator for producing a digital output count in accordance with said saw tooth generator output signal;

a digital-to-analog converter having an input coupled to the output of said divide by N counter for producing a signal at the output of said digital analog converter having a staircase waveform;

third circuit means for modulating the output signal of said digital-to-analog converter with a second sinusoidally varying signal phase shifted from said first sinusoidally varying signal and for energizing a scanning coil of said second pair of scanning coils in accordance with the sinusoidally modulated digital-to-analog converter output signal;

a second inverter having an input coupled to the output of said digital to analog converter for producing a signal at the output of said inverter which is phase shifted from the output signal of said digital to analog converter; and fourth circuit means for modulating the output signal of said second inverter with said second sinusoidally varying signal and for energizing said other of said scanning coils in accordance with the sinusoidally varying inverter output signal.

7. An improved nuclear magnetic resonance blood flowmeter for non-invasively measuring blood flow in a human limb comprising:

(a) polarizing magnet means for generating a substantially uniform magnetic field;

(b) a limb receiving lumen for supporting a human limb within the field generated by said polarizing magnet means so that blood molecules within the limb are magnetically polarized thereby;

(c) transmitter means located adjacent said lumen for inducing a nuclear magnetic resonance response in the blood molecules of the human limb disposed within said lumen, said transmitter means including:

i. a transmitter coil disposed about said lumen so that the field of said transmitter coil is oriented orthogonally to the magnetic field produced by said polarizing magnet means;

ii. a transmitter coupled to said transmitter coil for energizing said transmitter coil with a radio frequency signal;

iii. a modulator coil disposed about said lumen concentric with said transmitter coil but oriented so that the field of said modulator coil is orthogonal to the field of said transmitter coil and parallel to the magnetic field of said polarizing magnet means;

iv. a modulator for energizing said modulator coil with a signal whose frequency is substantially below the frequency of the transmitter;

v. a tag coil disposed about said lumen upstream of said transmitter and modulator coils, said tag coil being oriented so that the direction of its field is parallel to the field direction of said transmitter coil; and vi. radio frequency signal generating means for energizing said tag coil with a radio frequency signal to demagnetize a selected bolus of blood to enable downstream detection of the blood bolus by said detecting means so as to facilitate blood flow measurement;

(d) scanning means including:

i. first means for generating a first pair of opposing magnetic fields within said lumen for cancelling the nuclear magnetic resonance response induced by said transmitter means everywhere except within a first null plane along which said first opposing magnetic fields cancel each other;

ii. second means for generating a second pair of opposing magnetic fields which are each at a preselected angle to each of the magnetic fields of said first pair of opposing magnetic fields for cancelling the nuclear magnetic resonance response everywhere along a second null plane at which said second pair of opposing magnetic fields cancel each other, said second null plane being at said preselected angle to said first null plane so that a nuclear magnetic resonant response occurs only along a line formed by the intersection of said first and second null planes;

iii. control means coupled to said first and second means for generating said first and second pair of opposing magnetic fields for varying the strength of the opping magnetic fields generated by said first and second means for generating said first and second pair of opposing magnet fields to shift the location of said first and second null planes across said lumen so as to displace said line of intersection of said null planes through the human limb disposed in said lumen; and (e) detector means disposed in part in said lumen for detecting the nuclear magnetic resonance response induced in said lumen and for generating an output signal which varies in accordance with blood flow through said limb, said detector means including:

i. a receiver coil disposed about said lumen so that the direction of the field induced in said receiver coil is orthogonal to the field direction of said transmitter means to sense the magnetic resonance response induced by said transmitter means;

ii. a receiver coupled to said receiver coil for producing an intermediate frequency output signal varying in accordance with the nuclear magnetic resonance response induced in said receiver coil by said transmitter means;

iii. signal generator means for generating a reference intermediate frequency signal;

iv. a synchronous phase detector coupled to said receiver and to said signal generator means for detecting the induced nuclear magnetic resonant response in accordance with the phase difference between said receiver intermediate frequency signal and said reference intermediate frequency signal generated by said signal generator; and v. a filter and amplifier for filtering and amplifying the phase detector output signal to yield a signal at the output of said amplifier and filter which varies in accordance with the induced nuclear magnetic resonant response and hence blood flow; and wherein said radio frequency signal generating means for energizing said tag coil comprises:

a radio frequency oscillator for producing a radio frequency output signal; and a power amplifier for energizing said tag coil in accordance with the output signal of said radio frequency oscillator.

8. The blood flowmeter according to claim 7 further including a tag select circuit for periodically rendering said radio frequency signal oscillator operative and for disabling said phase detector means just before, during and just after said radio frequency signal generator means is enabled and for enabling said phase detector means during intervals other than said intervals just before, during and just after said radio frequency oscillator is enabled.

9. An improved nuclear magnetic resonance blood flowmeter for non-invasively measuring blood flow in a human limb comprising:

(a) a pair of polarizing permanent magnets for generating a substantially uniform magnetic field;

(b) a pair of electromagnetic coils each located on the pole face of a separate one of said magnets;

(c) a field controller circuit coupled to each of said electromagnetic coils for energizing said electromagnetic coils in response to the flux of said polarizing magnets;

(d) a limb-receiving lumen for supporting a human limb within the magnetic field generated by said polarizing magnets so that the blood molecules within the limb are magnetized thereby;

(e) transmitter means located adjacent said lumen for inducing a nuclear magnetic resonant response in the blood molecules of the human limb disposed within the said lumen;

(f) scanning means including:

i. a first pair of scanning coils for generating a pair of opposing magnetic fields within said lumen for cancelling the nuclear magnetic resonant response induced by said transmitter means everywhere except within a first null plane along which said opposing fields cancel each other;

ii. a second pair of scanning coils for generating a pair of opposing magnetic fields within said lumen which are each at a preselected angle to the fields of said first pair of opposing magnetic fields for cancelling induced nuclear magnetic response everywhere except along a second null plane at which said fields generated by said second pair of scanning coils cancel each other, said second null plane being at said preselected angle with said first null plane so that the only induced nuclear magnetic resonant response appears along a line formed by the intersection of said two null planes; and iii. a control circuit coupled to said first and second scanning coils for energizing each of the coils of said first and second pair of scanning coils with opposing currents of varying strength to vary the strength of the opposing magnetic fields generated by said first and second pair of scanning coils and thus shift the location of said first and second null planes across said lumen so as to displace said line of intersection of said null planes through the human limb disposed in said lumen; and (g) detector means disposed in part in said lumen for detecting nuclear magnetic resonant response induced in the blood of a limb and generating an output signal which varies in accordance with blood flow; and wherein said field controller circuit comprises:

a flux sensor disposed within the magnetic field generated by said polarizing magnets for producing an output signal which varies in accordance with the polarizing magnet flux;

means in thermal contact with said flux sensor for maintaining said flux sensor at a substantially constant temperature so as to stabilize said flux sensor output signal; and amplifier means having an input coupled to said flux sensor and having an output coupled to each of said pair of electromagnetic coils for energizing said electromagnetic coils in accordance with the output signal of said flux sensor.

10. The blood flowmeter according to claim 9 wherein said means for maintaining said flux sensor at a substantially constant temperature comprises:

a temperature-responsive element in thermal contact with said flux sensor for presenting an impedance thereacross whose magnitude varies in accordance with the flux sensor temperature;

a heater in thermal contact with said flux sensor; and amplifier means having an input coupled to said temperature responsive element and having an output coupled to said heater for energizing said heater in accordance with said temperature-responsive element impedance to maintain said flux sensor temperatures substantially constant.

11. The blood flowmeter according to claim 9 wherein said flux sensor comprises a Hall effect probe.

12. The blood flowmeter as recited in claim 9 which further includes:

(h) tagging means located adjacent said lumen upstream of said transmitter means for producing a bolus of blood, said tagging means comprising:

a tag coil disposed about said lumen upstream of said transmitting means, said tag coil oriented so that the direction of the tag coil field is parallel to the field radiated by said transmitter means;

a radio frequency oscillator for producing radio frequency output signal;

a power amplifier supplied at its input with the output signal of the radio frequency signal oscillator for energizing the tag coil in accordance with the radio frequency oscillator output signal; and a tag select circuit coupled to said radio frequency signal oscillator and coupled to said detector means for periodically rendering said radio frequency signal oscillator operative and for disabling said phase detector circuit for a predetermined interval just before, during and after said radio frequency oscillator is enabled and for disabling said radio frequency oscillator and for enabling said phase detector circuit during other intervals.

13. In a system which produces a controlled magnetic field, a thermally compensated flux sensor for providing a temperature-independent output signal for use in controlling the flux magnitude of the magnetic field comprising:

a flux sensor probe responsive to the flux of the magnetic field for producing said output signal which varies in accordance with the magnitude of the flux;

a temperature-responsive element in thermal contact with said flux sensor probe for presenting an impedance thereacross which varies in magnitude with the temperature of said flux sensor probe;

a heater in thermal contact with said flux sensor probe; and an amplifier coupled at its input to said temperature-responsive element and coupled at its output to said heater for energizing said heater in response to the impedance of said temperature-responsive element for maintaining the temperature of said flux sensor probe substantially constant.

14. The flux sensor according to claim 13 wherein said flux sensor probe is a Hall effect probe.

15. The flux sensor according to claim 14 wherein said heater comprises a power transistor.

16. A temperature-compensated circuit for maintaining the magnetic field produced by a pair of opposing magnets substantially constant comprising:

a pair of electromagnetic coils each located surrounding the pole face of a separate one of the pair of opposing magnets;

a flux sensor disposed within the magnetic field produced by the pair of opposing magnets for producing an output signal whose magnitude varies in accordance with the flux of the magnetic field produced by the opposing magnets;

a temperature-responsive element in thermal contact with said flux sensor for maintaining an impedance thereacross which varies in magnitude in accordance with the temperature of said flux sensor;

a heater in thermal contact with said flux sensor;

first amplifier means having an input coupled to said temperature-responsive element and an output coupled to said heater for energizing said heater in accordance with the impedance of said temperature-responsive element and second amplifier means having an input coupled to said flux sensor and having an output coupled to each of said electromagnetic coils for energizing said electromagnetic coils in accordance with the flux sensor output signal.

17. The circuit according to claim 16 wherein said flux sensor comprises a Hall effect probe.

18. A circuit according to claim 16 wherein said heater comprises a power transistor.

19. For use with a nuclear magnetic resonance blood flowmeter having a pair of spaced apart, oppositely poled polarizing magnets for generating a substantially uniform magnetic field therebetween, a limb receiving lumen for supporting a human limb within the field generated by the polarizing magnet so that the blood molecules within the limb are polarized thereby, transmitter means for inducing a nuclear magnetic resonance response in the blood molecules of the limb supported within the lumen; a tag coil carried by the lumen upstream of the transmitter, a tag signal generator for energizing the tag coil with a radio frequency signal, and detector means disposed in part in the lumen for detecting the nuclear magnetic resonance response induced in the lumen by the transmitter, the improvement comprising:

a tag select circuit coupled to the tag signal generator and to the detector means for periodically rendering the tag signal generator operative to energize the tag coil and to disable the detector means during the interval just before, during and just after the tag signal generator means is enabled and for enabling the detector means for disabling the tag signal generator means during other intervals.

20. The invention according to claim 19 wherein the tag select circuit comprises:

a signal generator for periodically generating an output pulse;

a first one shot multi-vibrator circuit having an input coupled to the output of said pulse generator for producing a signal of predetermined duration at its output each time said pulse generator generates an output pulse;

a buffer amplifier having an input coupled to the output of said first one shot multi-vibrator circuit and having an output coupled to the tag signal generator for rendering said tag signal generator operative during the duration of the output pulse of said first one shot multi-vibrator;

a second one shot multi-vibrator having an input coupled to the output of said first one shot multi-vibrator for producing a signal of a predetermined duration at the output of said second one shot multi-vibrator in response to the output signal of said first one shot multi-vibrator;

a first two input OR gate having its first input coupled to the output of said first one shot multi-vibrator and having its second input coupled to the output of said second one shot multi-vibrator for producing a high level logic voltage at its output during the duration of the output signal of said first one shot multi-vibrator and during the duration of the output signal of said second one shot multi-vibrator and;

a second two input OR gate having its first input coupled to the output of said first OR gate and having its second input coupled to the output of said pulse generator for supplying a signal to said phase detector means to render said phase detector inoperative when the signals at said first or second inputs is at a high logic level.

* * * * *